(12) United States Patent
Carter et al.

(10) Patent No.: US 7,183,253 B2
(45) Date of Patent: Feb. 27, 2007

(54) SUBSTANTIALLY PURE GLYCOPEPTIDE ANTIBIOTICS AC-98-1, AC-98-2, AC-98-3, AC-98-4 AND AC-98-5

(75) Inventors: Guy Thomas Carter, New City, NY (US); Haiyin He, Washington Township, NJ (US)

(73) Assignee: Wyeth Holdings Corp., Madison, NJ (US)

( * ) Notice: Subject to any disclaimer, the term of this patent is extended or adjusted under 35 U.S.C. 154(b) by 445 days.

(21) Appl. No.: 10/771,652

(22) Filed: Feb. 4, 2004

(65) Prior Publication Data

US 2004/0158035 A1   Aug. 12, 2004

Related U.S. Application Data

(62) Division of application No. 10/132,012, filed on Apr. 25, 2002, now Pat. No. 6,713,448.

(60) Provisional application No. 60/286,249, filed on Apr. 25, 2001, provisional application No. 60/286,244, filed on Apr. 25, 2001, provisional application No. 60/286,396, filed on Apr. 25, 2001.

(51) Int. Cl.
*A61K 38/16* (2006.01)
(52) U.S. Cl. .......................... 514/8; 435/118; 514/317
(58) Field of Classification Search ................... 514/8; 435/118; 530/317
See application file for complete search history.

(56) References Cited

U.S. PATENT DOCUMENTS

| 3,495,004 A | 2/1970 | De Voe et al. |
| 5,648,456 A | 7/1997 | Malabarba et al. |
| 5,939,523 A | 8/1999 | Bossi et al. |

FOREIGN PATENT DOCUMENTS

WO   PCT/US02/13073   9/2002

*Primary Examiner*—Herbert J. Lilling
(74) *Attorney, Agent, or Firm*—Daniel B. Moran

(57) ABSTRACT

The invention provides new substantially pure antibiotics designated AC-98-1, AC-98-2, AC-98-3, AC-98-4 and AC-98-5 derived from the microorganism *Streptomyces hygroscopicus*.

12 Claims, 15 Drawing Sheets

SUBSTANTIALLY PURE GLYCOPEPTIDE ANTIBIOTICS AC-98-1, AC-98-2, AC-98-3, AC-98-4 AND AC-98-5

CROSS REFERENCE TO RELATED APPLICATIONS

This application is a divisional application of copending application, application Ser. No. 10/132,012 filed Apr. 25, 2002 now U.S. Pat. No. 6,713,448 which claims priority from provisional applications Application No. 60/286,396 filed on Apr. 25, 2001, Application No. 60/286,244, filed on Apr. 25, 2001, Application Number 60/286,249 filed Apr. 25, 2001. These applications are herein incorporated by reference in their entireties.

BACKGROUND OF THE INVENTION

1. Field of the Invention

This invention relates to new substantially pure glycopeptide antibiotics, designated AC-98-1, AC-98-2, AC-98-3, AC-98-4 and AC-98-5, or pharmaceutically acceptable salts thereof, to methods for the preparation and isolation of such antibiotics, to methods of utilizing such antibiotics to treat bacterial infections and to pharmaceutical compositions containing such antibiotics.

2. Description of the Prior Art

U.S. Pat. No. 3,495,004 discloses a producing organism *Streptomyces hygroscopicus* NRRL 3085, and production conditions to prepare a complex mixture of antibiotics AC-98. No details of the structures of the individual antibiotics are disclosed. As described in U.S. Pat. No. 3,495,004, the mixture of AC98 antibiotics could not be separated into single components by ion exchange (IRC-50), gel filtration (CM-sephadex), or normal phase chromatography (deactivated silica gel).

SUMMARY OF THE INVENTION

New substantially pure glycopeptide antibiotics designated AC-98-1, AC-98-2, AC-98-3, AC-98-4 and AC-98-5 or pharmaceutically acceptable salts thereof have now been found.

The structure of AC-98-1 is:

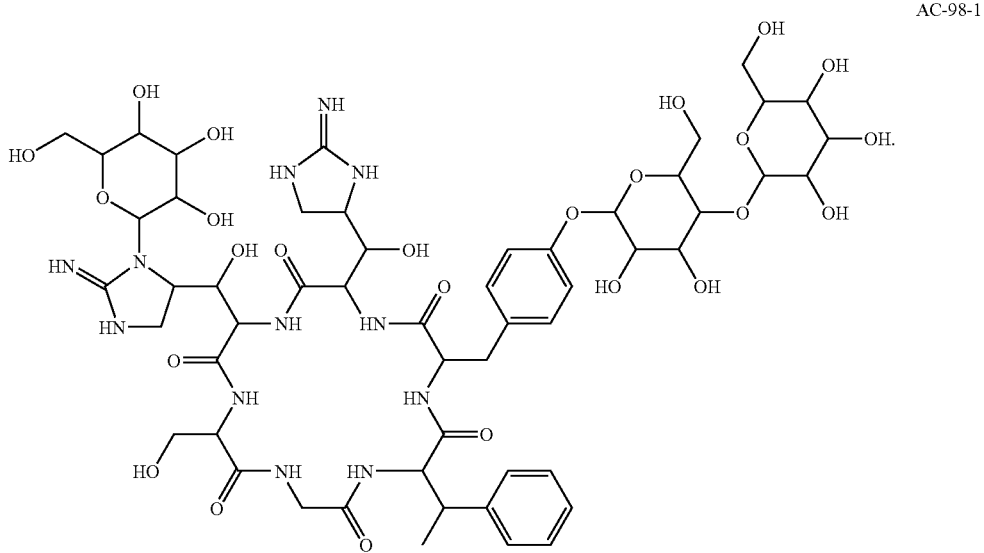

AC-98-1

Figure 1:
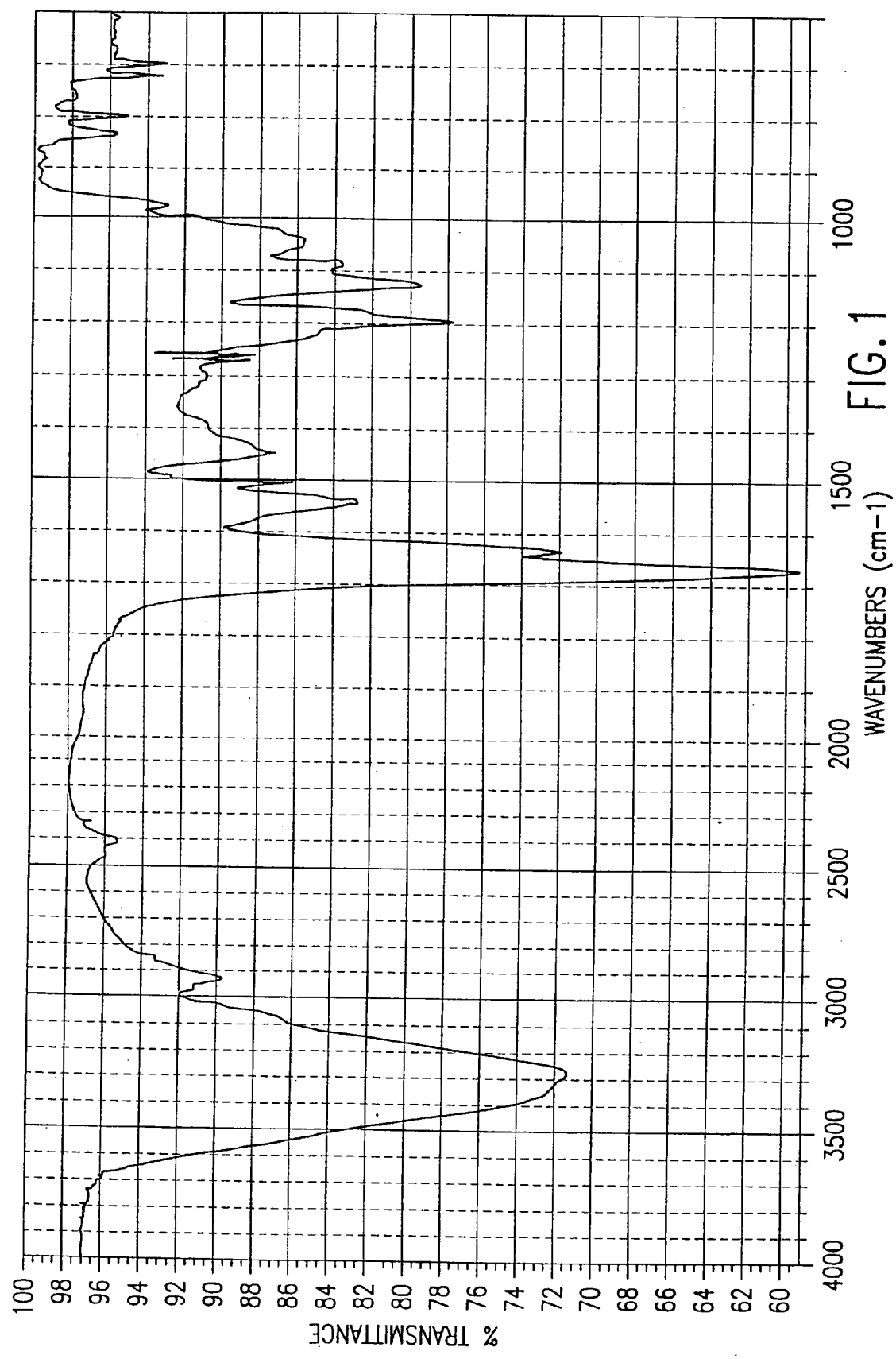
FIG. 1 shows the infrared absorption spectrum of AC-98-1
Figure 6:
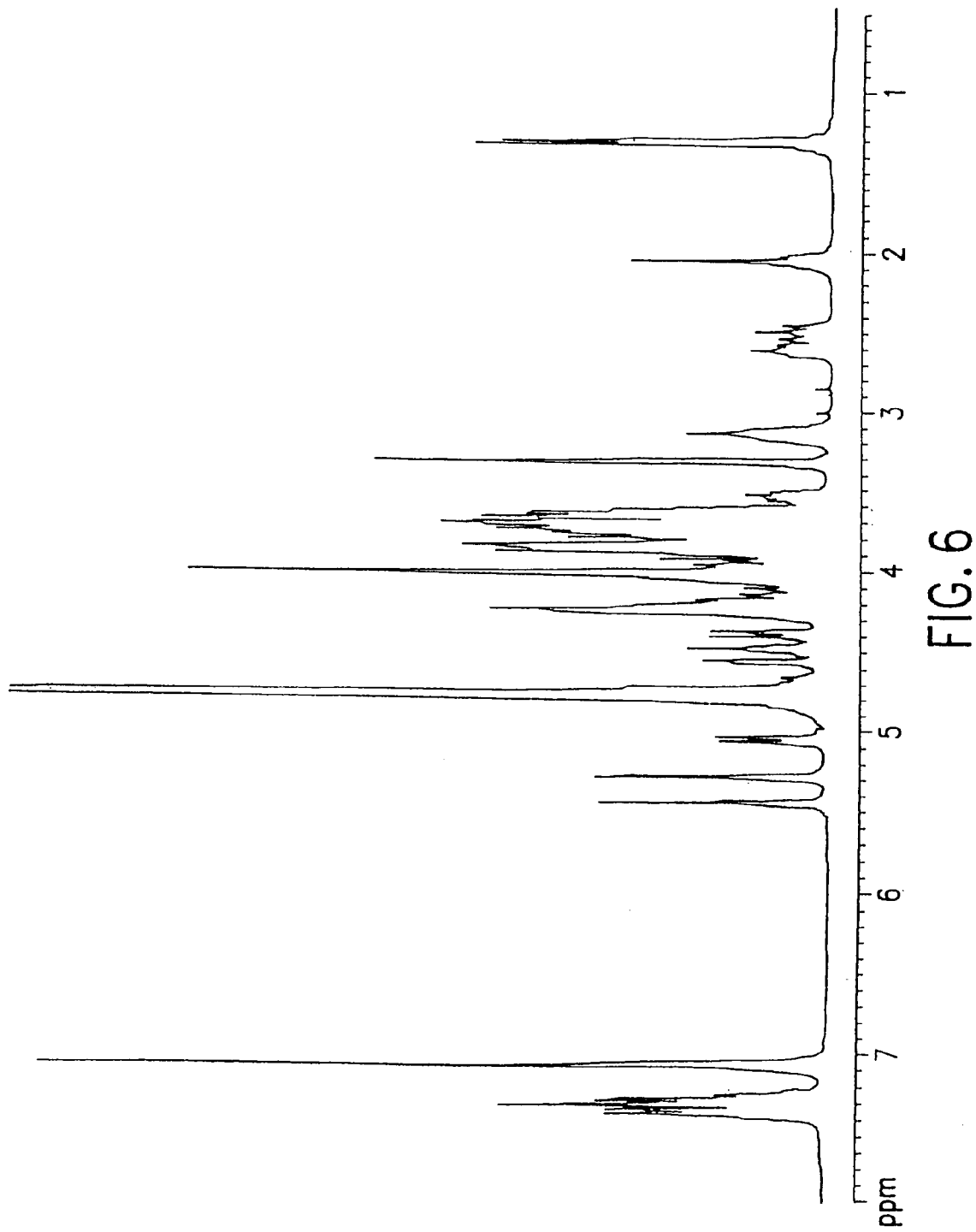
FIG. 6 shows the proton nuclear magnetic resonance spectrum of AC-98-1
Figure 11:
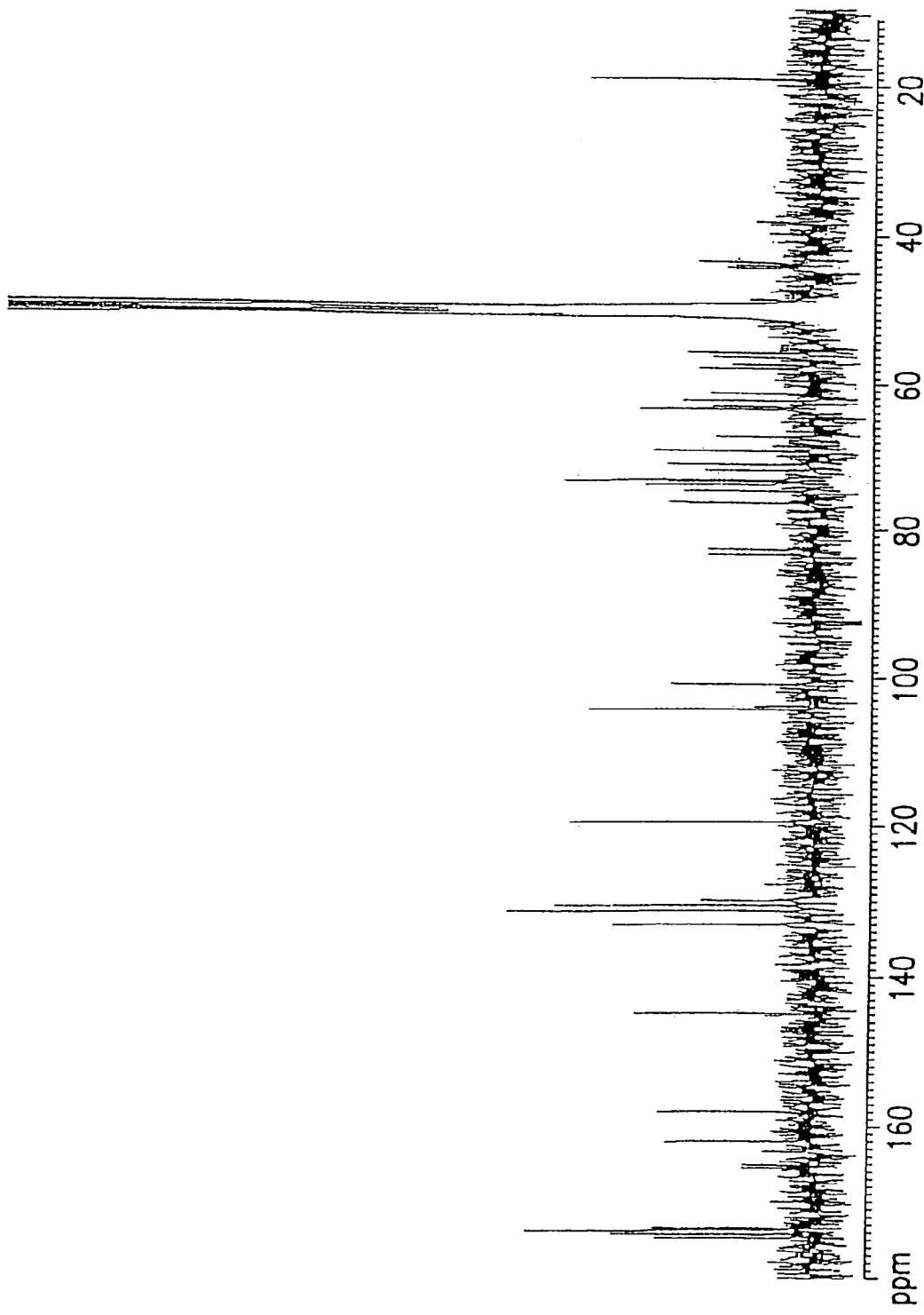
FIG. 11 shows the carbon-13 nuclear magnetic resonance spectrum of AC-98-1

The physico chemical characteristics of AC-98-1 are as follows:

a) Apparent Molecular Formula: $C_{54}H_{78}N_{12}O_{25}$ b) Molecular Weight: MS(ESI) $[M+2H]^{2+}$=M/Z 648 (m.w.=1292) HRFABMS calcd. for $C_{54}H_{78}N_{12}O_{25}Na$=M/Z 1317.5099 HRFABMS observed=M/Z 1317.5164 Δ mmu=6.5 c) Ultraviolet Absorption Spectrum: $\lambda_{max}$ nm MeOH=280, 273, 201;

d) Infrared Absorption Spectrum: as shown in FIG. 1 (KBr disk): 3374, 3277, 1681, 1634, 1554, 1510 $cm^{-1}$;

e) Proton Magnetic Resonance Spectrum: as shown in FIG. 6 (300 MHz, CD$_3$OD/D$_2$O 1:1)

f) Carbon-13 Nuclear Magnetic Resonance Spectrum: as shown in FIG. 11 (75 MHz, CD$_3$OD/D$_2$O 1:1), significant peaks are listed below (δ from TMS);

---
174.4, 173.9, 173.5, 173.5, 173.2, 173.0, 161.9,
161.7, 157.8, 144.8, 133.1, 133.0,
131.3, 130.5, 129.8, 119.4, 104.3, 100.8, 83.5,
82.7, 76.6, 76.4, 74.9, 74.1, 73.7,
73.5, 73.5, 73.3, 72.2, 72.0, 71.3, 69.5, 67.6,
63.8, 63.8, 63.8, 63.5, 62.7, 61.8, 58.3,
58.3, 57.8, 56.8, 56.1, 45.0, 44.8, 44.6, 44.1,
38.7, 19.9.

---

The structure of AC-98-2 is:

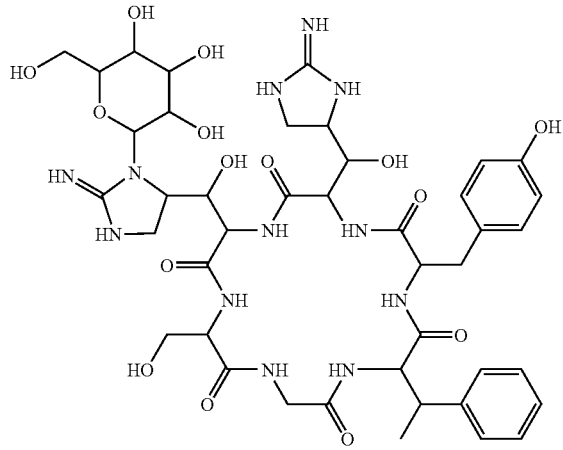

AC-98-2

Figure 2:
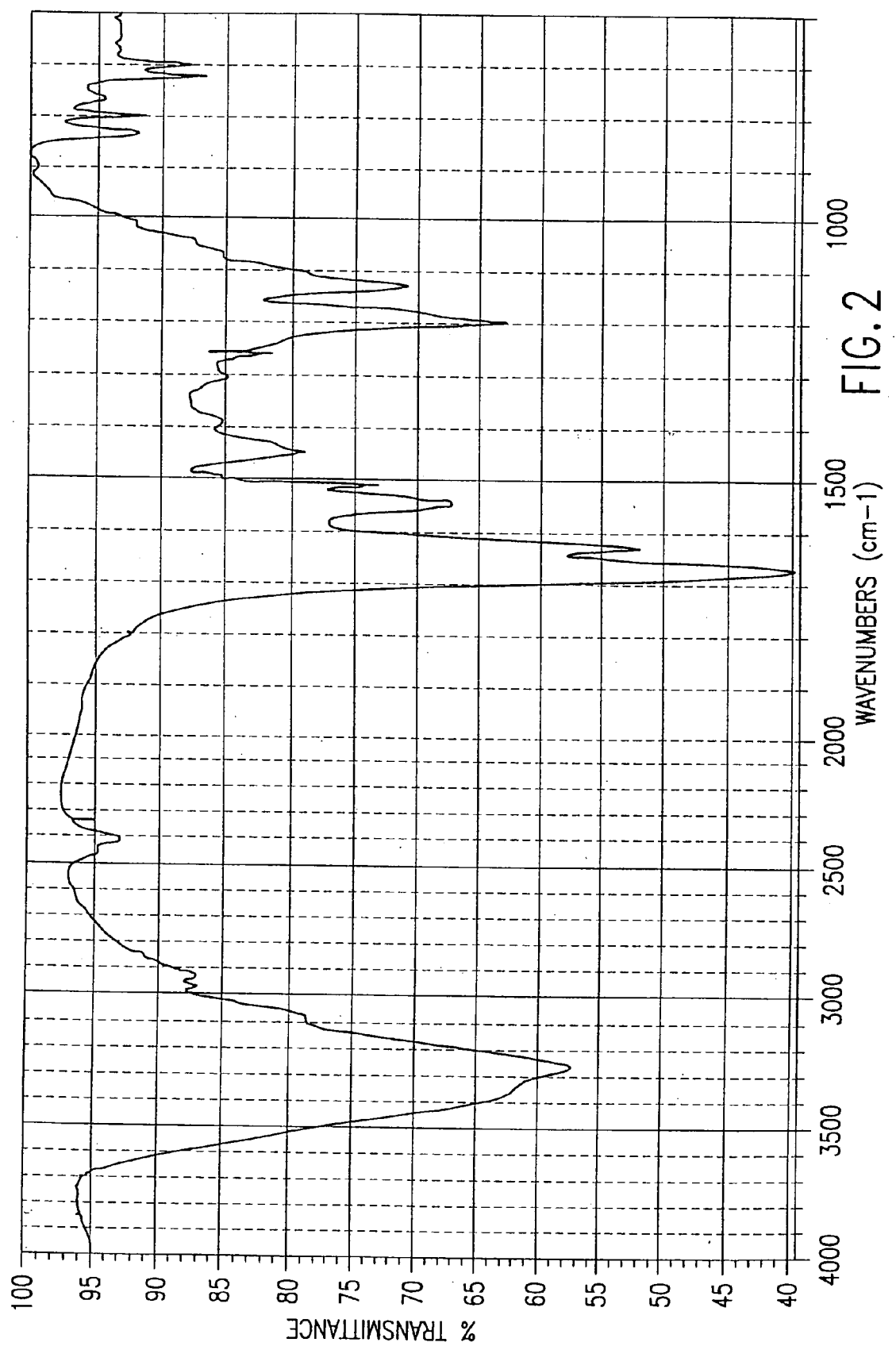
FIG. 2 shows the infrared absorption spectrum of AC-98-2
Figure 7:
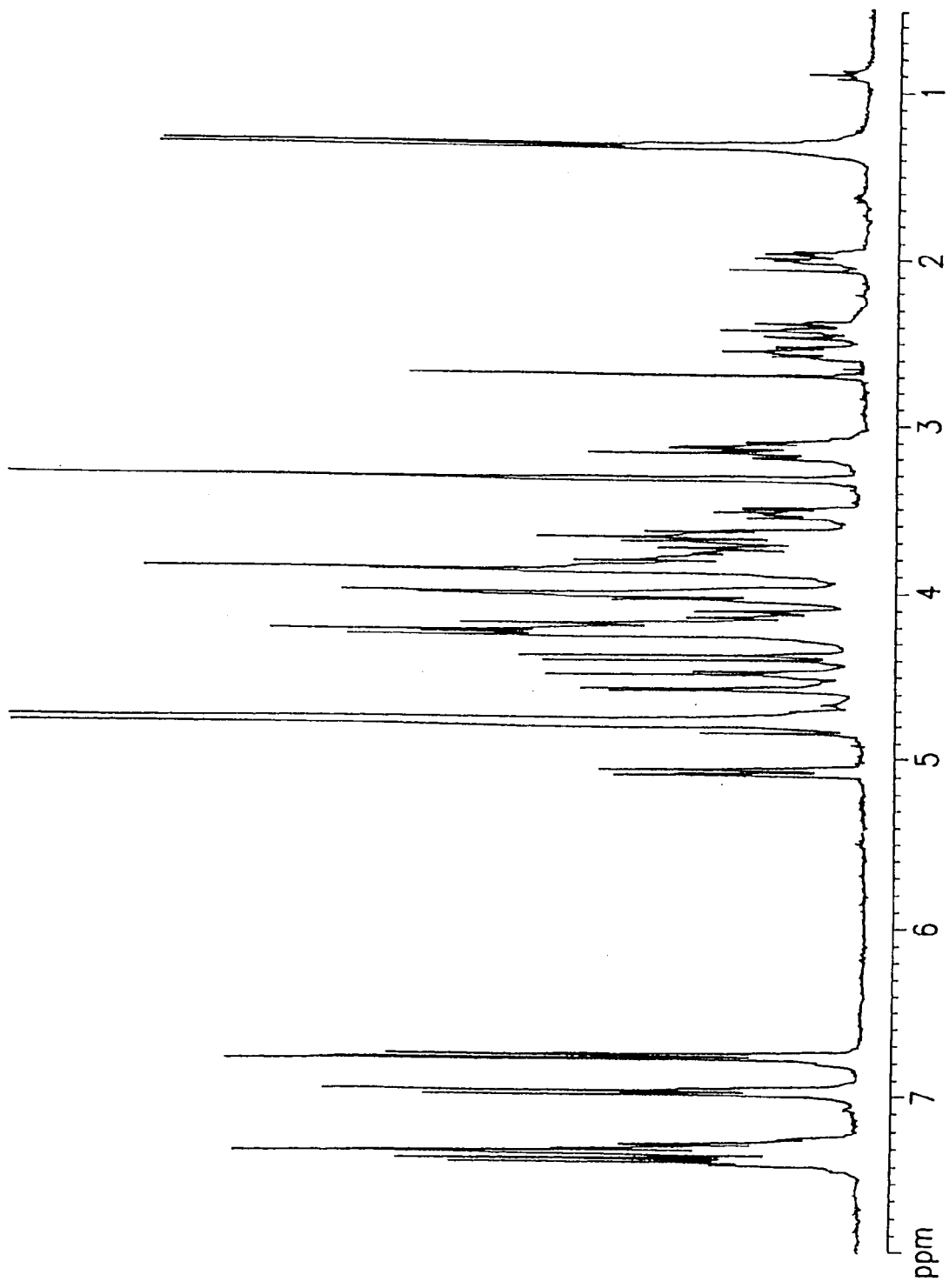
FIG. 7 shows the proton nuclear magnetic resonance spectrum of AC-98-2
Figure 12:
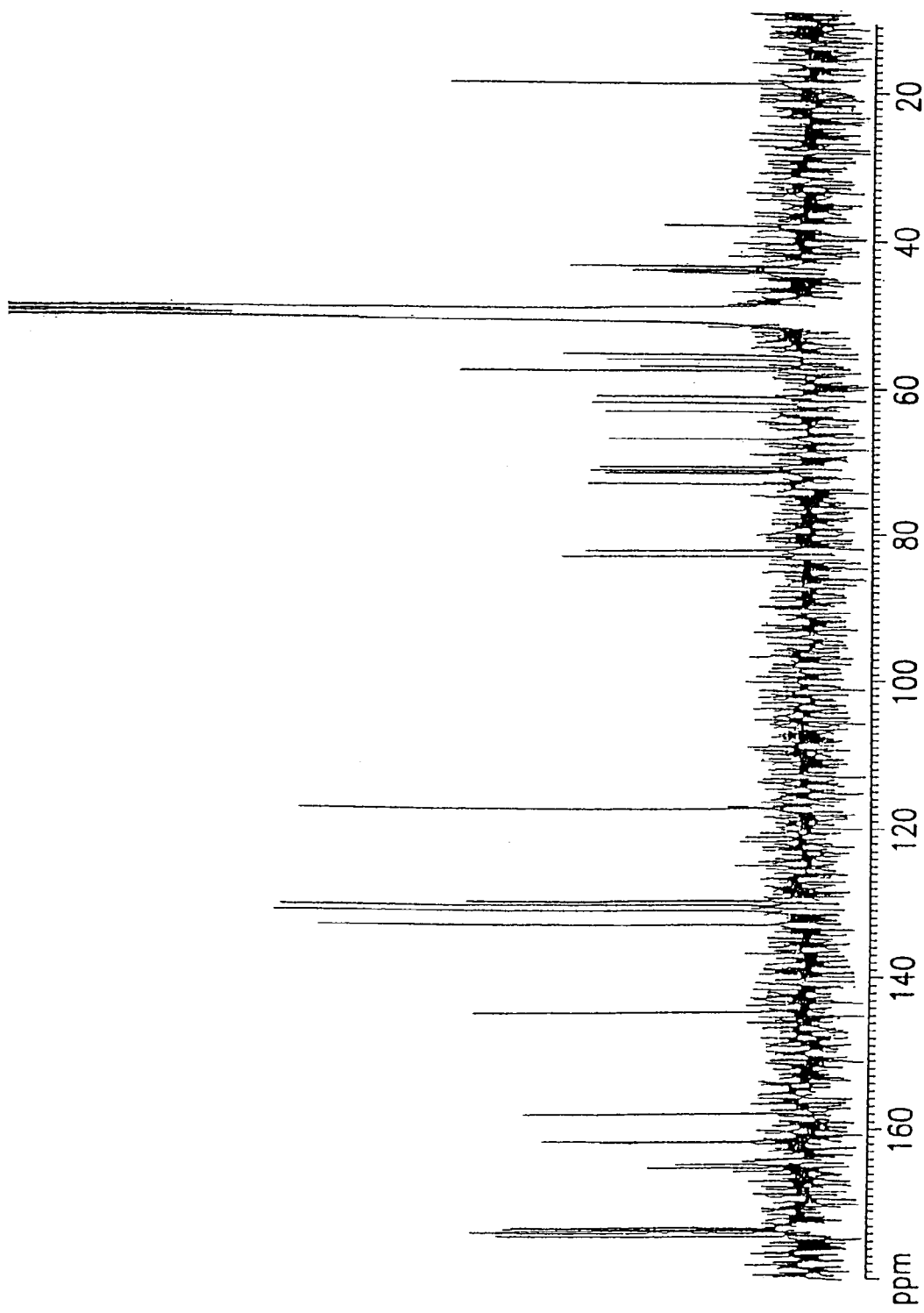
FIG. 12 shows the carbon-13 nuclear magnetic resonance spectrum of AC-98-2

The physico chemical characteristics of AC-98-2 are as follows:

a) Apparent Molecular Formula: C$_{42}$H$_{58}$N$_{12}$O$_{15}$ b) Molecular Weight: MS(ESI) [M+2H]$^{2+}$=M/Z 486 (m. w.=970) HRFABMS calcd. for C$_{42}$H$_{58}$N$_{12}$O$_{15}$Na=M/Z 992.4077 HRFABMS observed=M/Z 993.4042 Δ mmu=3.5 c) Ultraviolet Absorption Spectrum: λ$_{max}$ nm MeOH=280, 273, 201;

d) Infrared Absorption Spectrum: as shown in FIG. 2 (KBr disk): 3374, 3277, 1681, 1634, 1554, 1510 cm$^{-1}$;

e) Proton Magnetic Resonance Spectrum: as shown in FIG. 7 (300 MHz, CD$_3$OD/D$_2$O 1:1)

f) Carbon-13 Nuclear Magnetic Resonance Spectrum: as shown in FIG. 12 (75 MHz, CD$_3$OD/D$_2$O 1:1), significant peaks are listed below (δ from TMS);

---
174.3, 173.9, 173.5, 173.6, 173.2, 173.0, 162.0,
161.7, 158.2, 144.7, 133.1, 130.0,
131.3, 130.5, 129.8, 117.8, 83.5, 82.8, 73.7,
72.2, 71.9, 71.3, 67.6, 63.8, 63.8, 62.8,
61.8, 58.3, 58.3, 57.8, 56.8, 56.1, 45.1, 44.8,
44.5, 44.2, 38.7, 19.7.

---

The structure of AC-98-3 is:

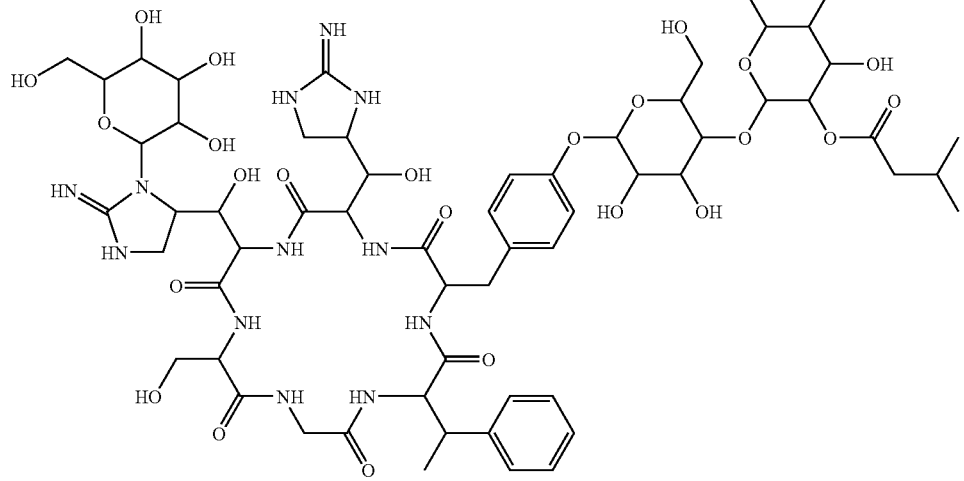

AC-98-3

Figure 3:
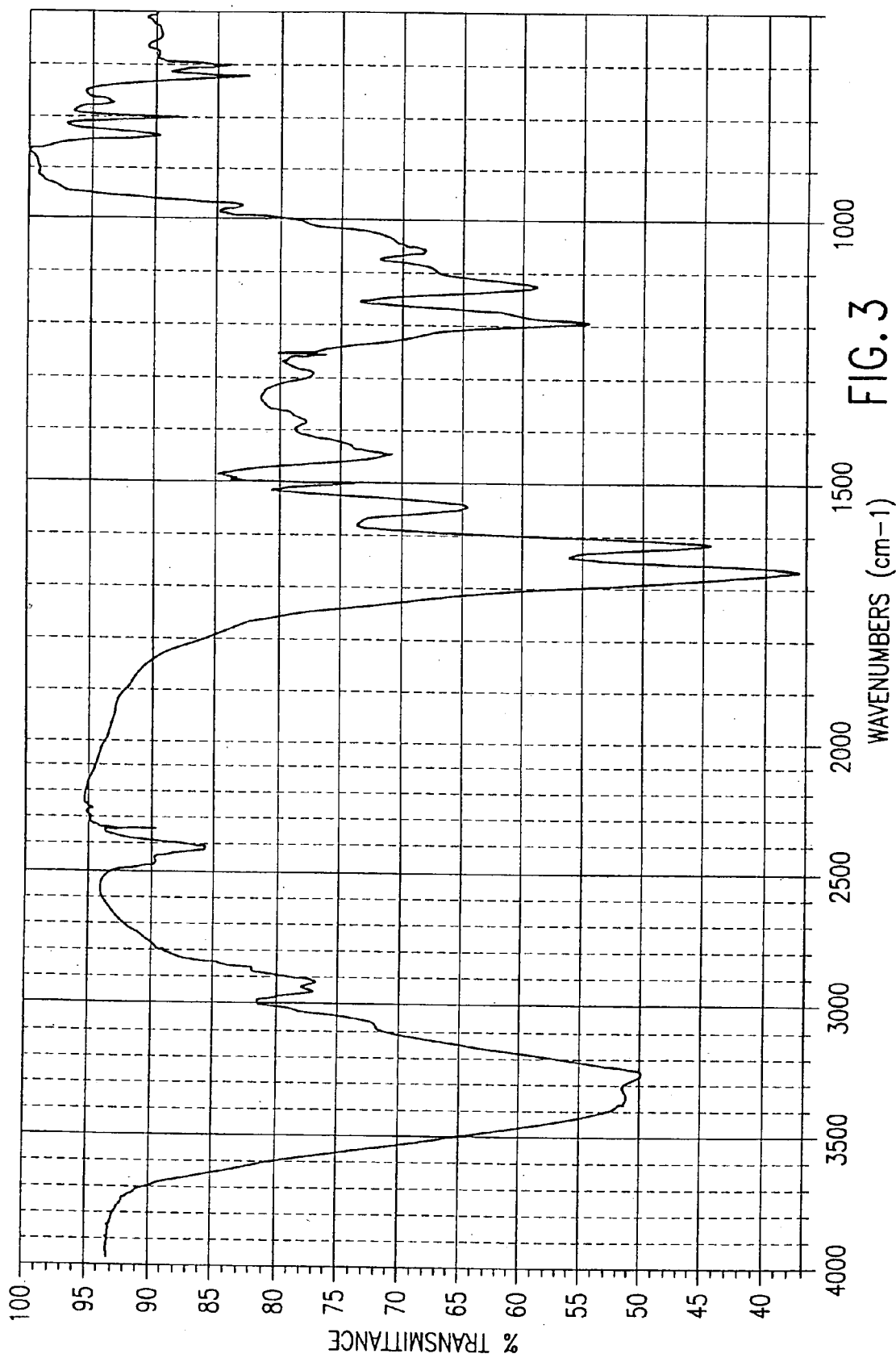
FIG. 3 shows the infrared absorption spectrum of AC-98-3
Figure 8:
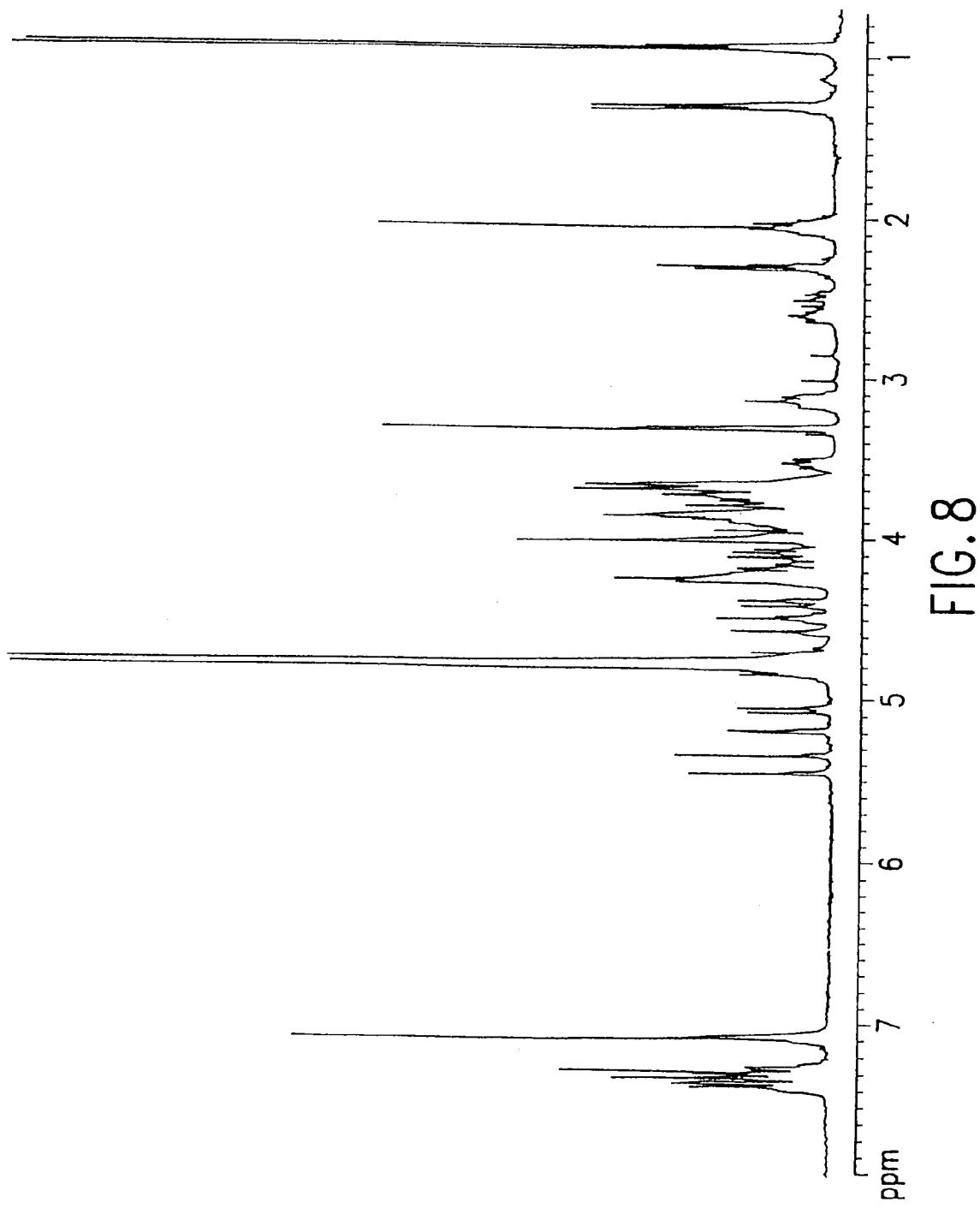
FIG. 8 shows the proton nuclear magnetic resonance spectrum of AC-98-3
Figure 13:
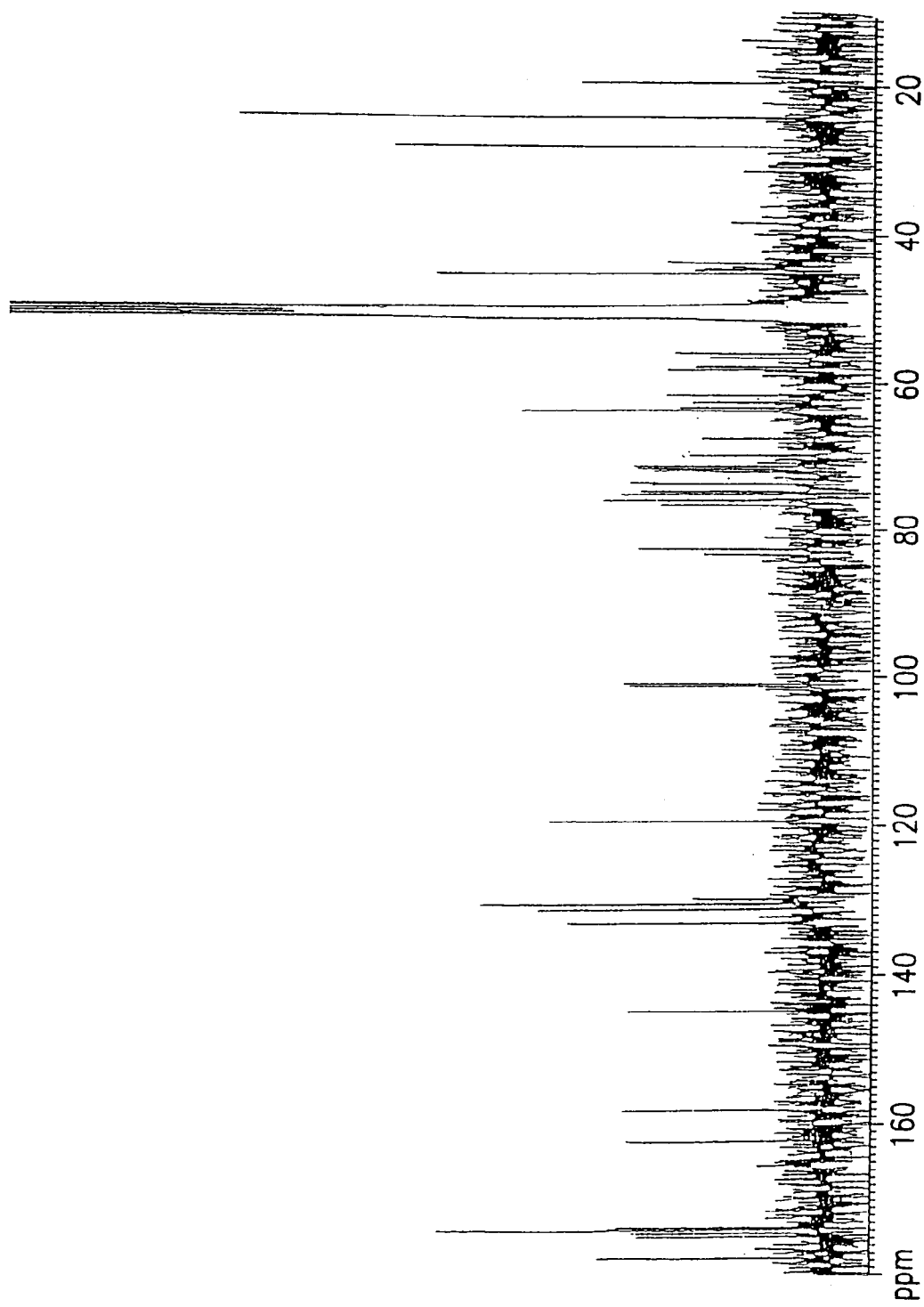
FIG. 13 shows the carbon-13 nuclear magnetic resonance spectrum of AC-98-3

The physico chemical characteristics of AC-98-3 are as follows:

a) Apparent Molecular Formula: $C_{59}H_{86}N_{12}O_{26}$
b) Molecular Weight: MS(ESI) $[M+2H]^{2+}$=M/Z 690 (m.w.=1378) HRFABMS calcd. for $C_{59}H_{87}N_{12}O_{26}$=M/Z 1379.5854 HRFABMS observed=M/Z 1379.5861 Δ mmu=0.5
c) Ultraviolet Absorption Spectrum: $\lambda_{max}$ nm MeOH=280, 273, 201;
d) Infrared Absorption Spectrum: as shown in FIG. 3 (KBr disk): 3374, 3277, 1681, 1634, 1554, 1510 cm$^{-1}$;
e) Proton Magnetic Resonance Spectrum: as shown in FIG. 8 (300 MHz, $CD_3OD/D_2O$ 1:1)
f) Carbon-13 Nuclear Magnetic Resonance Spectrum: as shown in FIG. 13 (75 MHz, $CD_3OD/D_2O$ 1:1), significant peaks are listed below (δ from TMS);

177.3, 174.4, 173.9, 173.5, 173.5, 173.2, 173.0,
161.9, 161.7, 157.8, 144.8, 133.2,
133.1, 131.2, 130.5, 129.8, 119.4, 101.2, 100.8,
83.5, 82.8, 76.7, 75.2, 74.8, 73.9,
73.7, 73.6, 71.7, 76.4, 72.2, 72.0, 71.3, 69.9,
67.6, 63.9, 63.8, 63.8, 63.5, 62.7, 61.8,
58.4, 58.3, 57.8, 56.8, 56.1, 45.0, 44.8, 44.6,
44.1, 38.7, 19.7, 45.6, 28.2, 24.27,
24.24.

Figure 4:
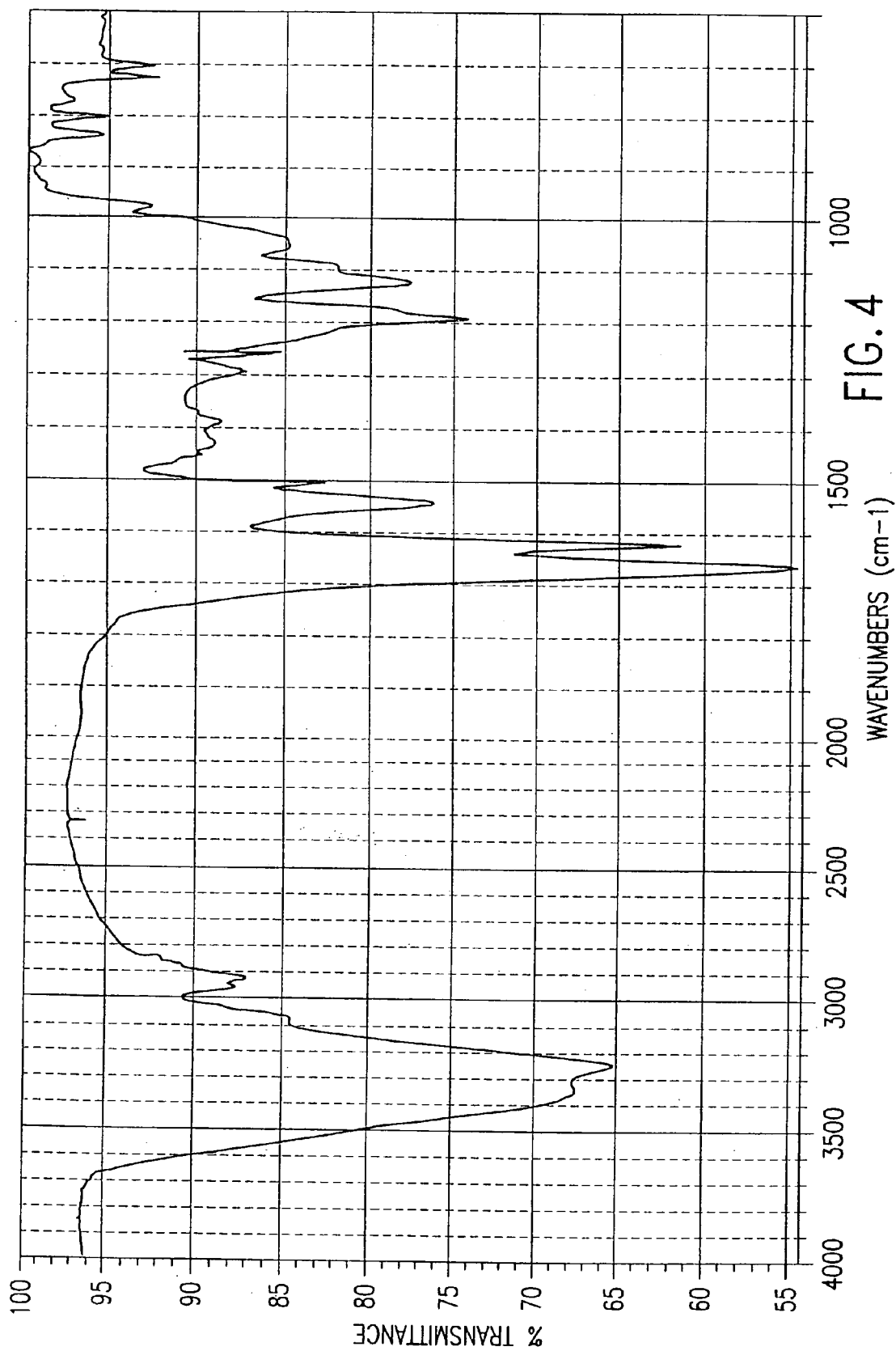
FIG. 4 shows the infrared absorption spectrum of AC-98-4
Figure 9:
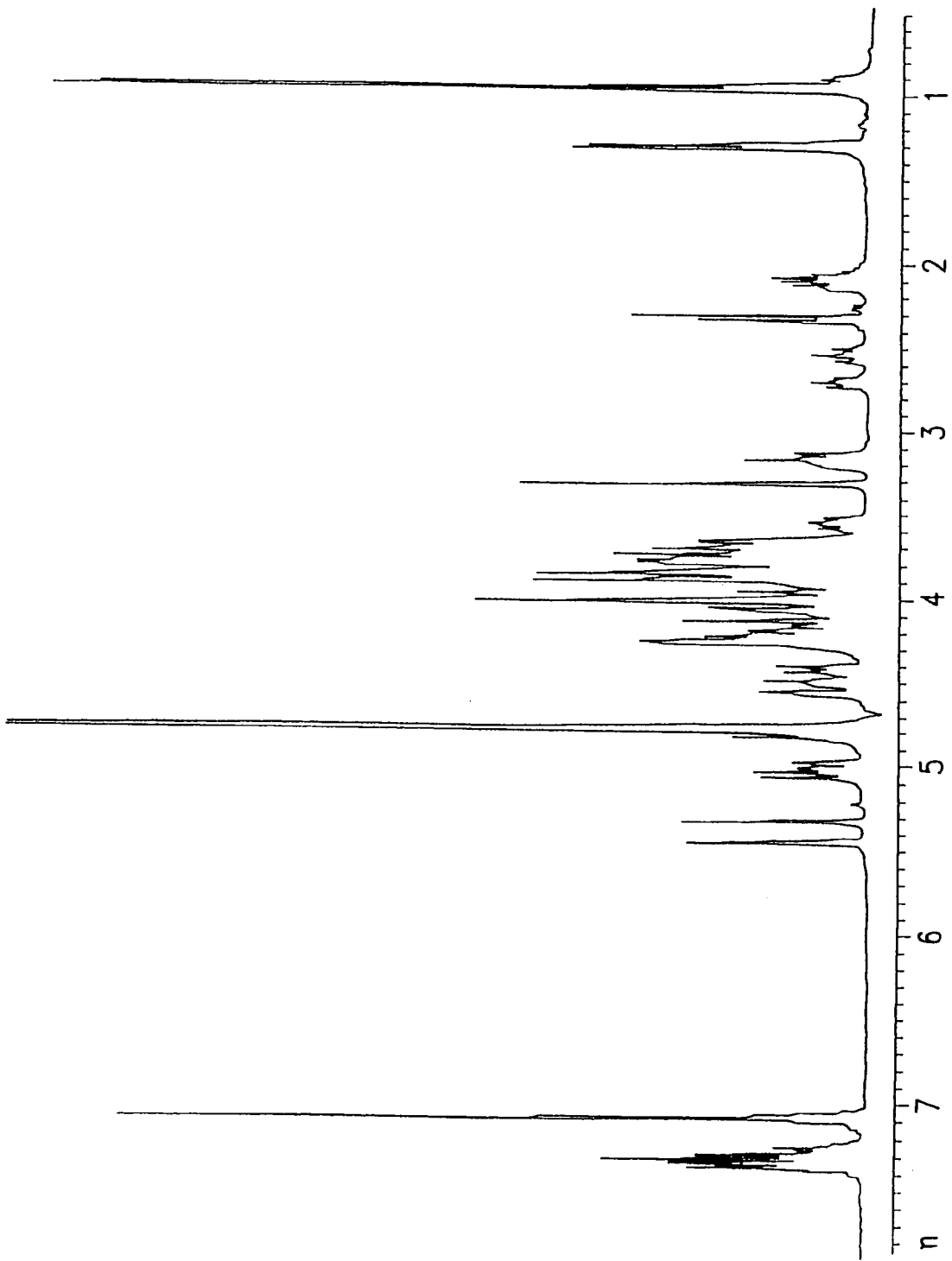
FIG. 9 shows the proton nuclear magnetic resonance spectrum of AC-98-4
Figure 14:
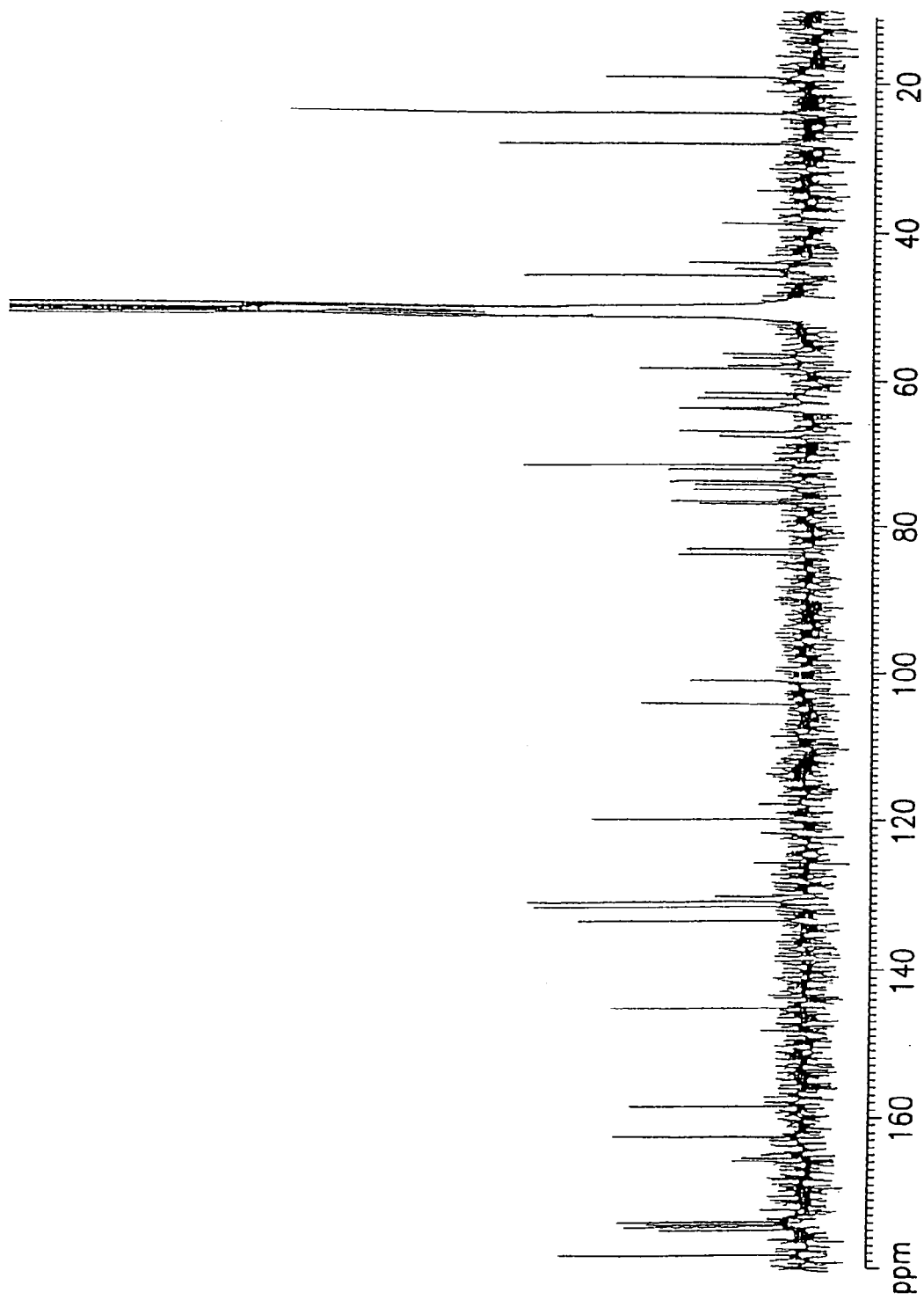
FIG. 14 shows the carbon-13 nuclear magnetic resonance spectrum of AC-98-4

The physico chemical characteristics of AC-98-4 are as follows:

a) Apparent Molecular Formula: $C_{59}H_{86}N_{12}O_{26}$
b) Molecular Weight: MS(ESI) $[M+2H]^{2+}$=M/Z 690 (m.w.=1378) HRFABMS calcd. for $C_{59}H_{87}N_{12}O_{26}$=M/Z 1379.5854 HRFABMS observed=M/Z 1379.5879 Δ mmu=2.5
c) Ultraviolet Absorption Spectrum: $\lambda_{max}$ nm MeOH=280, 273, 201;
d) Infrared Absorption Spectrum: as shown in FIG. 4 (KBr disk): 3374, 3277, 1681, 1634, 1554, 1511 cm$^{-1}$;
e) Proton Magnetic Resonance Spectrum: as shown in FIG. 9 (300 MHz, $CD_3OD/D_2O$ 1:1)
f) Carbon-13 Nuclear Magnetic Resonance Spectrum: as shown in FIG. 14 (75 MHz, $CD_3OD/D_2O$ 1:1), significant peaks are listed below (δ from TMS);

174.4, 173.9, 173.5, 173.6, 173.2, 173.0, 161.8,
161.8, 158.0, 144.9, 133.2, 133.1,
131.2, 130.5, 129.8, 119.5, 104.1, 101.1, 83.7,
82.8, 76.6, 76.9, 75.0, 74.2, 73.8,
73.6, 76.4, 71.4, 72.1, 72.1, 71.4, 67.0,
67.6, 63.8, 63.8, 63.9, 63.7, 62.7, 61.8, 58.4,
58.4, 57.9, 56.9, 56.3, 45.1, 44.9,
44.7, 44.1, 38.8, 19.6, 177.6, 45.8, 28.3, 24.3.

The structure of AC-98-4 is:

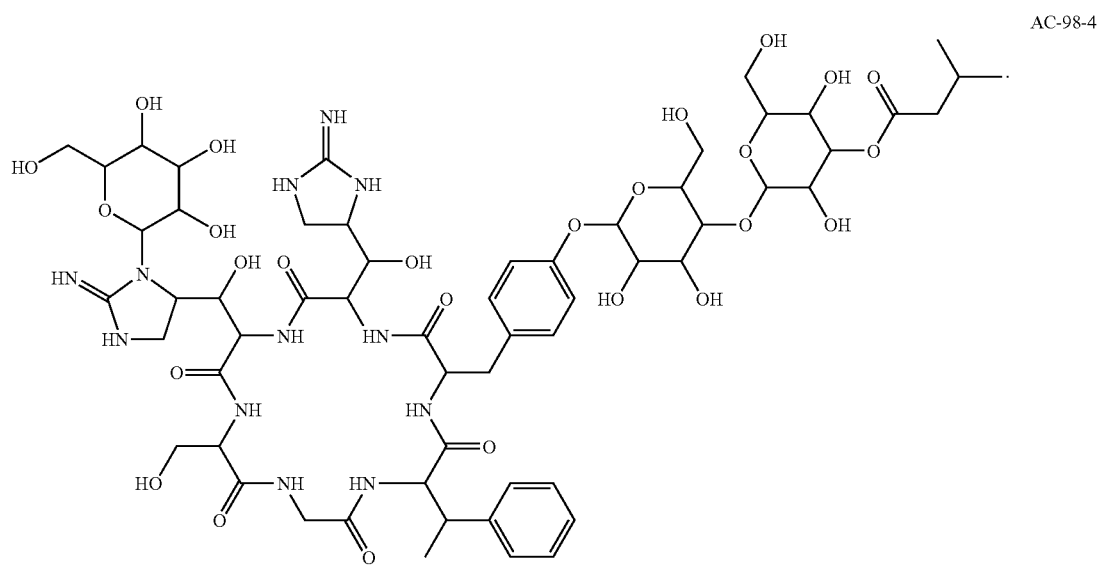

The structure of AC-98-5 is:

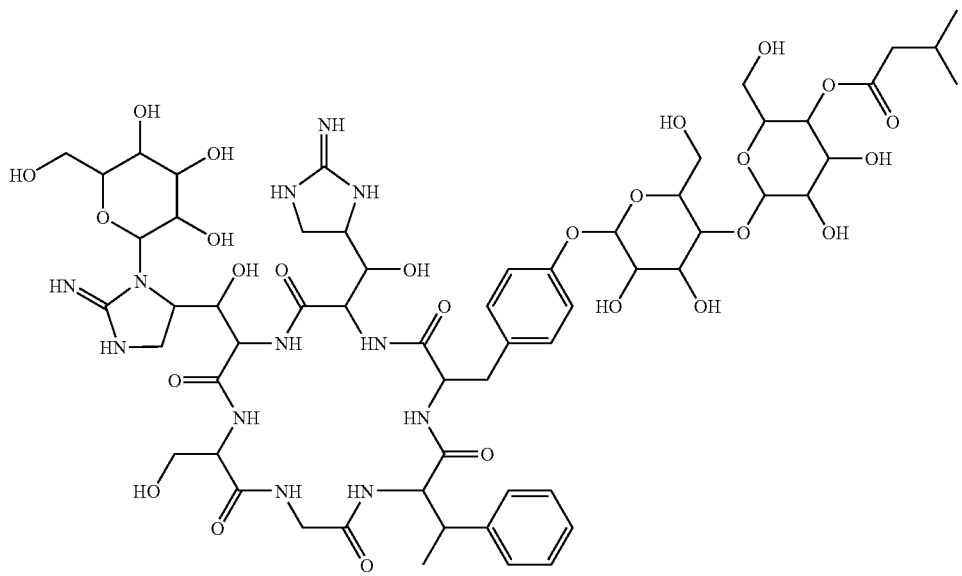

AC-98-5

Figure 5:
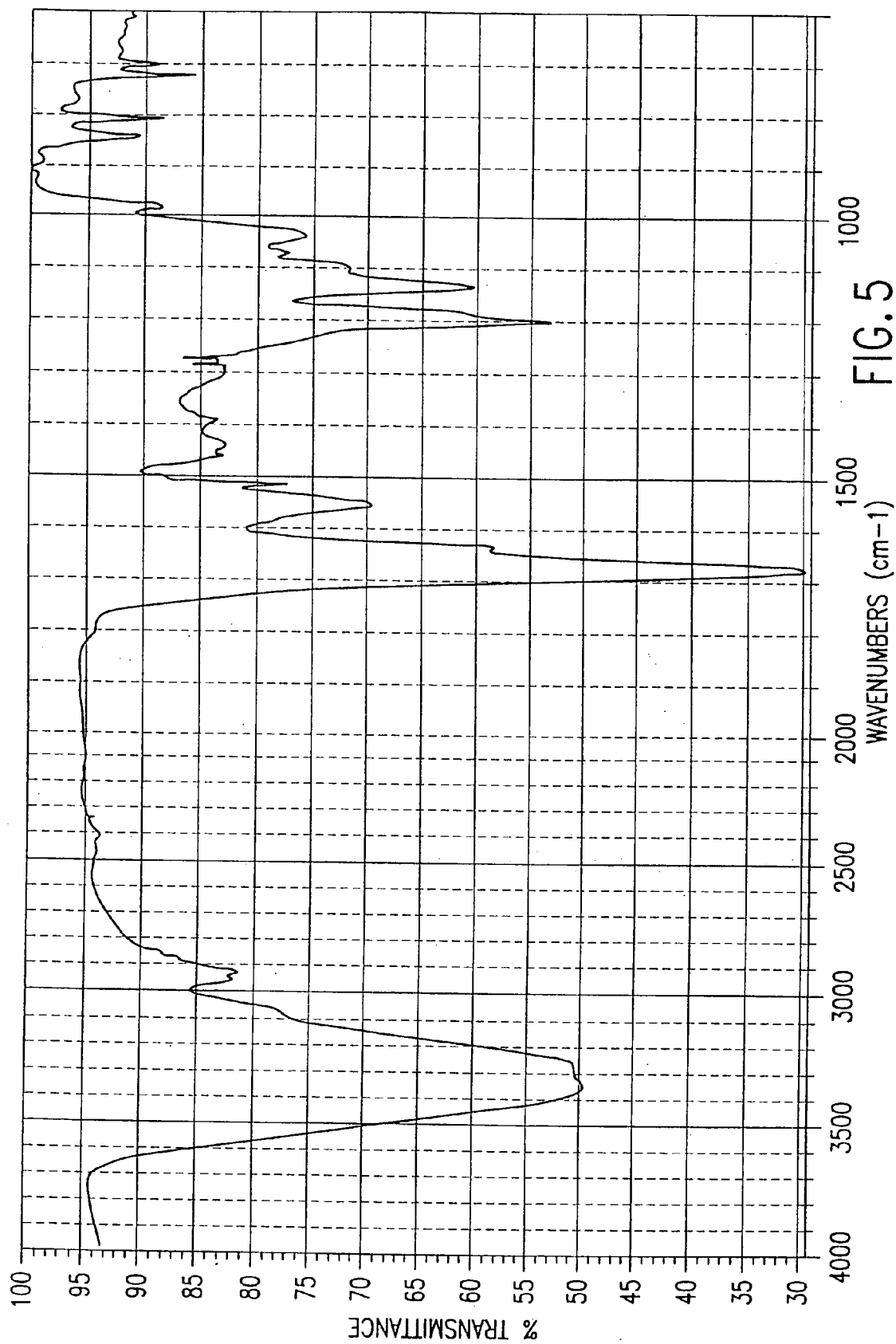
FIG. 5 shows the infrared absorption spectrum of AC-98-5
Figure 10:
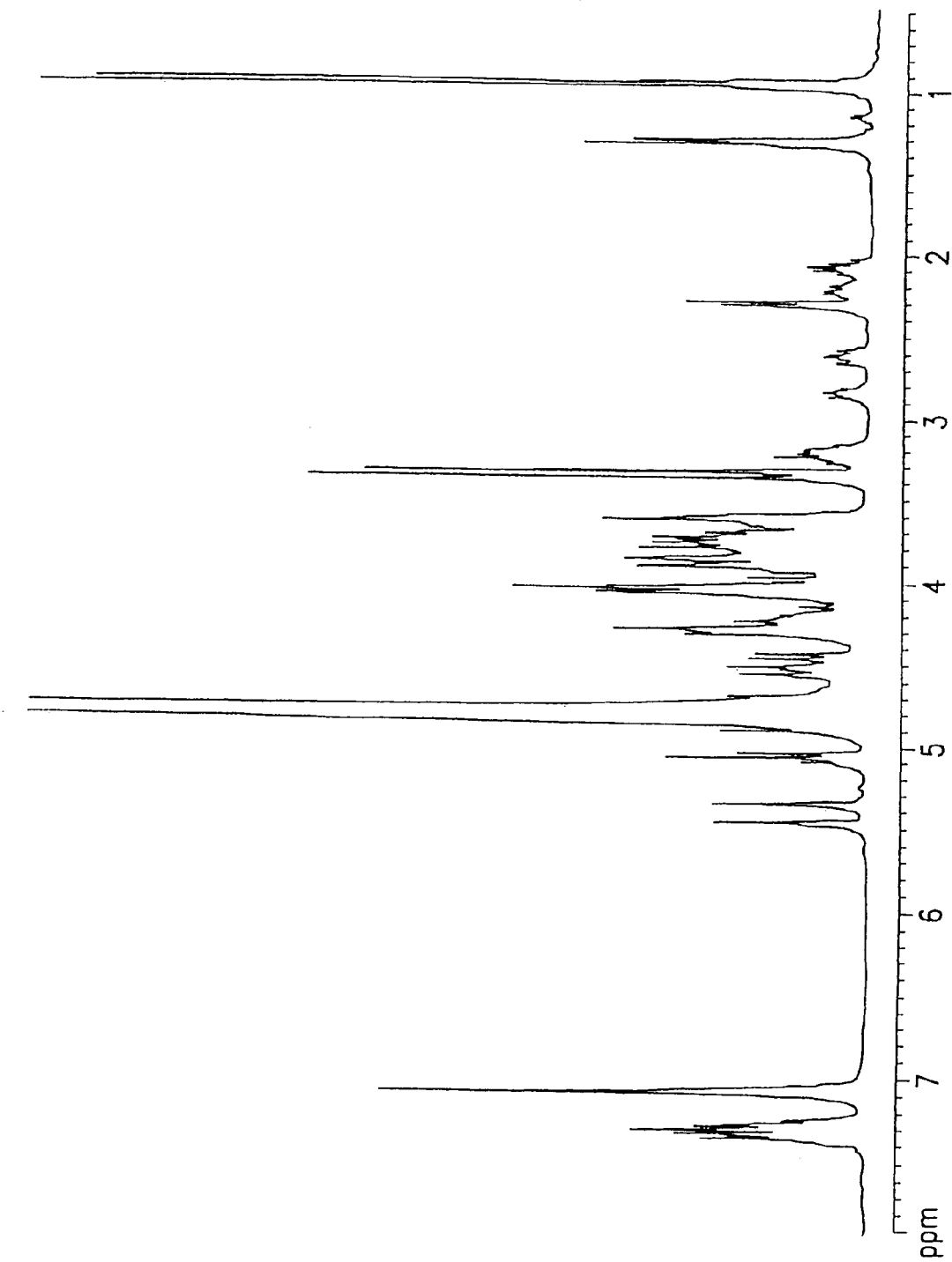
FIG. 10 shows the proton nuclear magnetic resonance spectrum of AC-98-5
Figure 15:
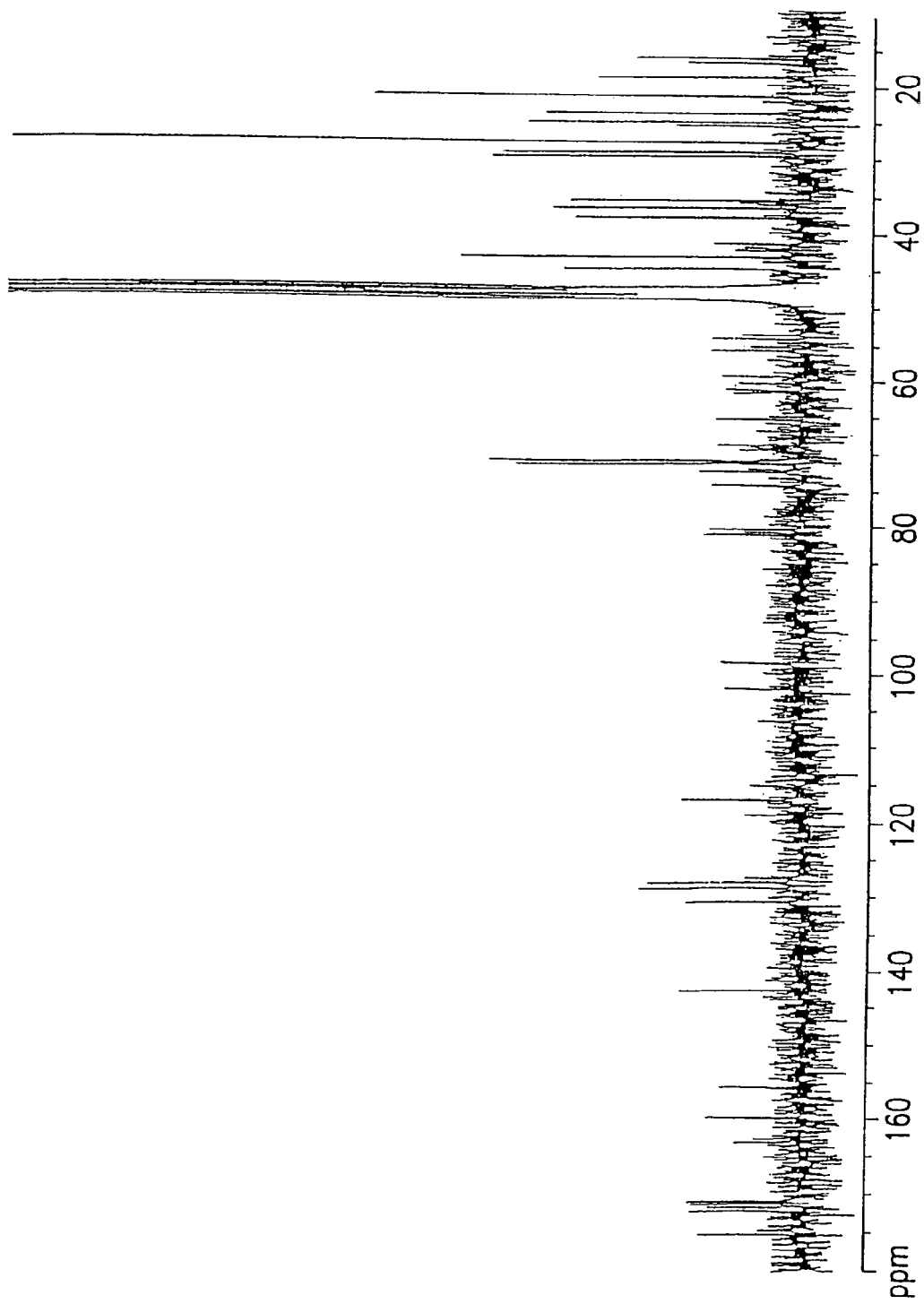
FIG. 15 shows the carbon-13 nuclear magnetic resonance spectrum of AC-98-5

The physico chemical characteristics of AC-98-5 are as follows:
  a) Apparent Molecular Formula: $C_{59}H_{86}N_{12}O_{26}$
  b) Molecular Weight: MS(ESI) $[M+2H]^{2+}$=M/Z 690 (m.w.=1378) HRFABMS calcd. for $C_{59}H_{86}N_{12}O_{26}Na$=M/Z 1401.5674 HRFABMS observed=M/Z 1401.5693 Δ mmu=1.9
  c) Ultraviolet Absorption Spectrum: $\lambda_{max}$ nm MeOH=280, 273, 201;
  d) Infrared Absorption Spectrum: as shown in FIG. 5 (KBr disk): 3374, 3277, 1681, 1634, 1554, 1510 cm$^{-1}$;
  e) Proton Magnetic Resonance Spectrum: as shown in FIG. 10 (300 MHz, $CD_3OD/D_2O$ 1:1)
  f) Carbon-13 Nuclear Magnetic Resonance Spectrum: as shown in FIG. 15 (75 MHz, $CD_3OD/D_2O$ 1:1), significant peaks are listed below (δ from TMS);

177.1, 174.7, 173.9, 173.6, 173.7, 173.3, 173.1,
162.1, 161.9, 157.9, 144.9, 133.1,
133.1, 131.2, 130.5, 129.7, 119.4, 104.3, 101.0,
83.9, 82.9, 76.7, 74.7, 75.0, 74.2,
73.9, 73.6, 71.8, 73.7, 72.3, 72.1, 71.6, 72.0,
67.7, 63.8, 63.8, 63.9, 64.3, 62.6, 61.9,
58.5, 58.6, 58.0, 57.0, 56.5, 45.1, 45.0, 44.8,
44.0, 38.8, 19.5, 45.9, 28.3, 24.36,
24.33.

In particular the structures of substantially pure AC-98-1, AC-98-2, AC-98-3, AC-98-4 and AC-98-5 are:

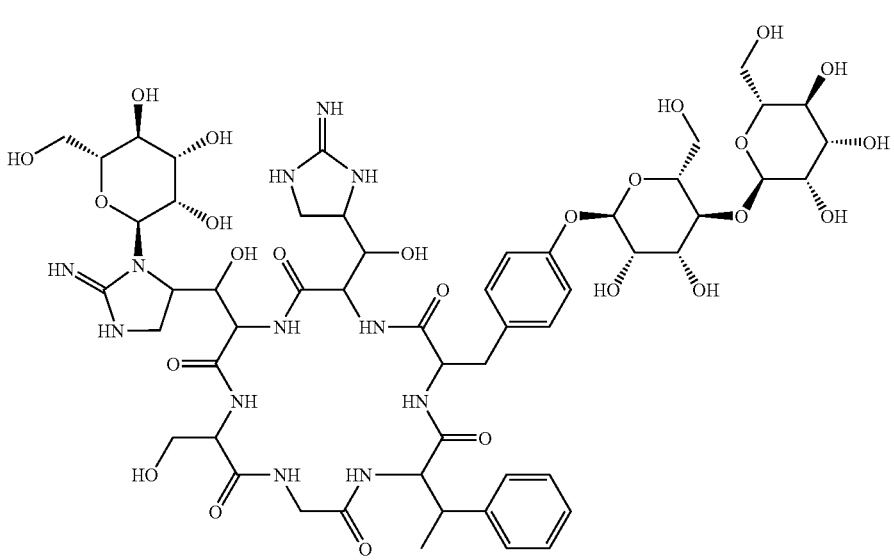

AC-98-1

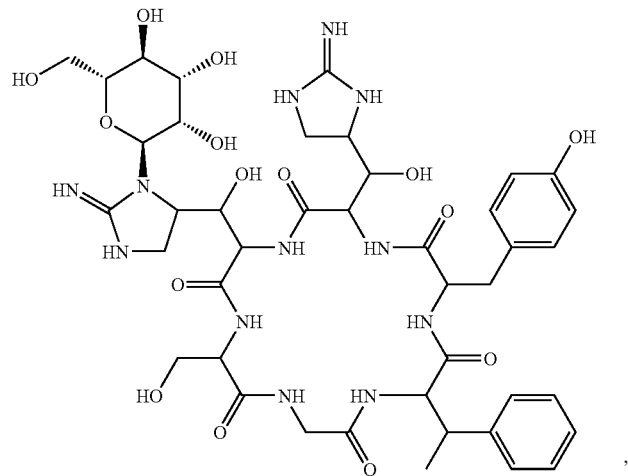
AC-98-2
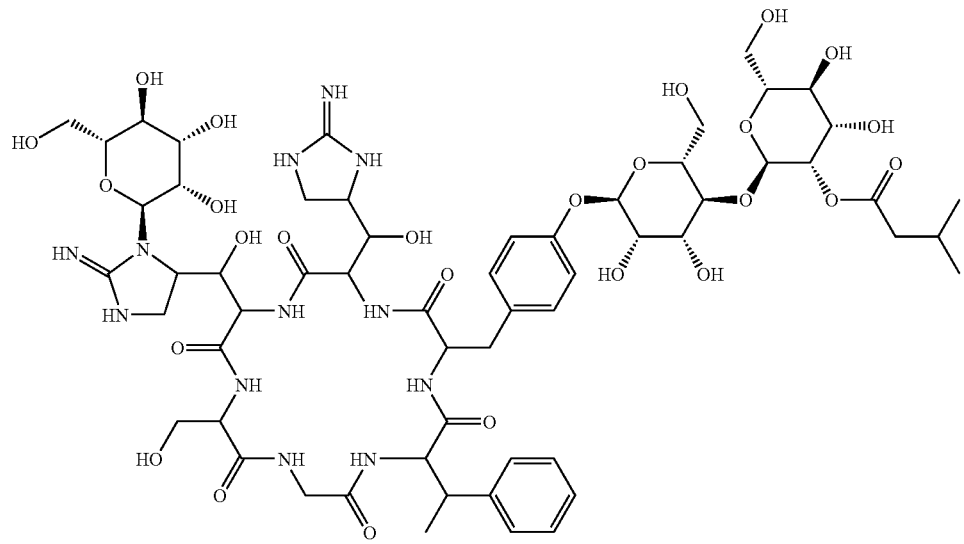
AC-98-3
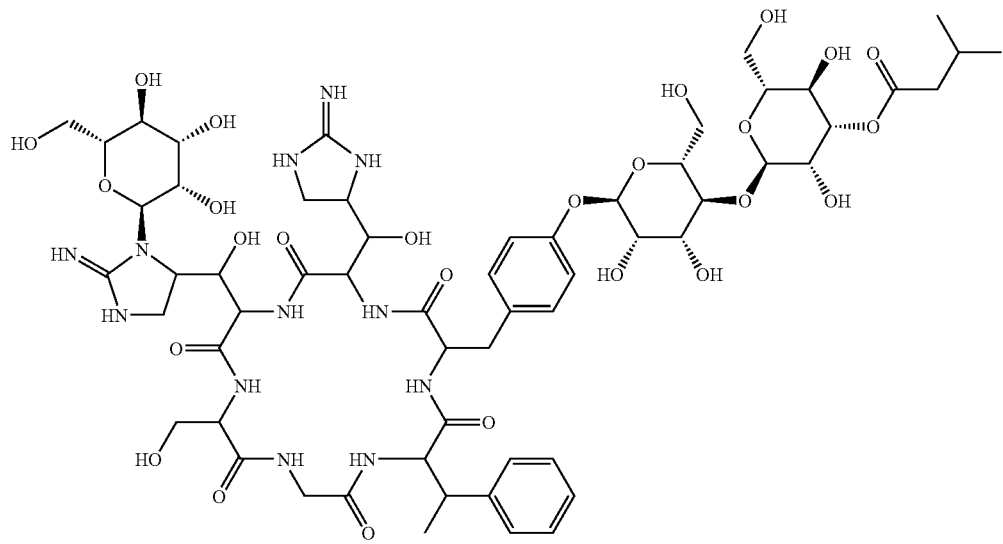
AC-98-4
and

-continued

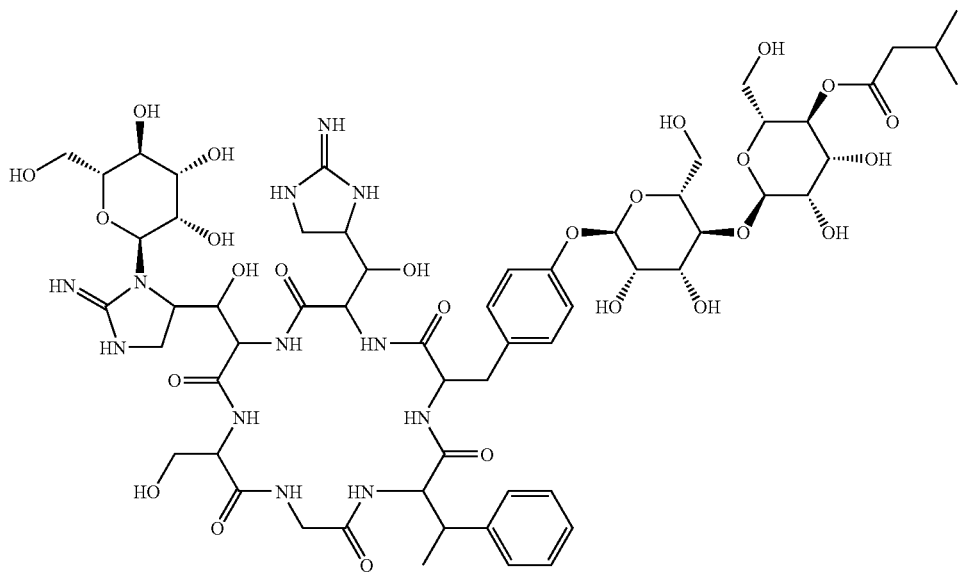

AC-98-5

This invention provides a method of preparing, separating and isolating substantially pure glycopeptide antibiotics AC-98-1, AC-98-2, AC-98-3, AC-98-4, and AC-98-5 from a recovered complex mixture.

This invention further provides a method for preparing substantially pure glycopeptide antibiotic AC-98-1 comprising the steps of:
  a. cultivating a suitable producing strain of *Streptomyces hygroscopicus* in a suitable culture medium under aerobic conditions to produce a mixture of AC-98 antibiotics containing AC-98-1;
  b. recovering said mixture of AC-98 antibiotics containing AC-98-1; and
  c. separating and isolating substantially pure AC-98-1 as the trifluoroacetic acid salt by reverse phase high pressure liquid chromatography with a mobile phase gradient of about 11% to about 25% acetonitrile in water containing about 0.02% trifluoroacetic acid.

Also preferred is a mobile phase gradient of about 40% to about 60% methanol in water containing about 0.02% trifluoroacetic acid.

This invention further provides a method for preparing substantially pure glycopeptide antibiotic AC-98-2 comprising the steps of:
  a. cultivating a suitable a producing strain of *Streptomyces hygroscopicus* in a suitable culture medium under aerobic conditions to produce a mixture of AC-98 antibiotics containing AC-98-2;
  b. recovering said mixture of AC-98 antibiotics containing AC-98-2; and
  c. separating and isolating substantially pure AC-98-2 as the trifluoroacetic acid salt by reverse phase high pressure liquid chromatography with a mobile phase gradient of about 11% to about 25% acetonitrile in water containing about 0.02% trifluoroacetic acid.

Also preferred is a mobile phase gradient of about 40% to about 60% methanol in water containing about 0.02% trifluoroacetic acid.

This invention further provides a method for preparing substantially pure glycopeptide antibiotic AC-98-3 comprising the steps of:
  a. cultivating a suitable producing strain of *Streptomyces hygroscopicus* in a suitable culture medium under aerobic conditions to produce a mixture of AC-98 antibiotics containing AC-98-3;
  b. recovering said mixture of AC-98 antibiotics containing AC-98-3; and
  c. separating and isolating substantially pure AC-98-3 as the trifluoroacetic acid salt by reverse phase high pressure liquid chromatography with a mobile phase gradient of about 11% to about 25% acetonitrile in water containing about 0.02% trifluoroacetic acid.

Also preferred is a mobile phase gradient of about 40% to about 60% methanol in water containing about 0.02% trifluoroacetic acid.

This invention further provides a method for preparing substantially pure glycopeptide antibiotic AC-98-4 comprising the steps of:
  a. cultivating a suitable producing strain of *Streptomyces hygroscopicus* in a suitable culture medium under aerobic conditions to produce a mixture of AC-98 antibiotics containing AC-98-4;
  b. recovering said mixture of AC-98 antibiotics containing AC-98-4; and
  c. separating and isolating substantially pure AC-98-4 as the trifluoroacetic acid salt by reverse phase high pressure liquid chromatography with a mobile phase gradient of about 11% to about 25% acetonitrile in water containing about 0.02% trifluoroacetic acid.

Also preferred is a mobile phase gradient of about 40% to about 60% methanol in water containing about 0.02% trifluoroacetic acid.

This invention further provides a method for preparing substantially pure glycopeptide antibiotic AC-98-5 comprising the steps of:

a. cultivating a suitable producing strain of *Streptomyces hygroscopicus* in a suitable culture medium under aerobic conditions to produce a mixture of AC-98 antibiotics containing AC-98-5;
b. recovering said mixture of AC-98 antibiotics containing AC-98-5; and
c. separating and isolating substantially pure AC-98-5 as the trifluoroacetic acid salt by reverse phase high pressure liquid chromatography with a mobile phase gradient of about 11% to about 25% acetonitrile in water containing about 0.02% trifluoroacetic acid.

Also preferred is a mobile phase gradient of about 40% to about 60% methanol in water containing about 0.02% trifluoroacetic acid.

It is understood that this invention encompasses all crystalline forms of substantially pure glycopeptide antibiotics AC-98-1, AC-98-2, AC-98-3, AC-98-4 and AC-98-5. Further, substantially pure antibiotics AC-98-1, AC-98-2, AC-98-3, AC-98-4 and AC-98-5 may be obtained as pharmaceutically acceptable salts which are those derived from such organic and inorganic acids as: acetic, trifluoroacetic, lactic, citric, tartaric, formate, succinic, maleic, malonic, gluconic, hydrochloric, hydrobromic, phosphoric, nitric, sulfuric, methanesulfonic, and similarly known acceptable acids. The pharmaceutically acceptable salts of compounds of the invention are prepared using conventional procedures.

Substantially pure compounds of the invention have centers of asymmetry. The substantially pure compounds may, therefore, exist in at least two and often more stereoisomeric forms. The present invention encompasses all stereoisomers of the substantially pure compounds whether free from other stereoisomers or admixed with other stereoisomers in any proportion and thus includes, for instance, racemic mixtures of enantiomers as well as the diastereomeric mixtures of isomers. The absolute configuration of any substantially pure compound may be determined by any suitable method including conventional X-ray crystallography.

The present invention accordingly provides a pharmaceutical composition which comprises a substantially pure glycopeptide antibiotic AC-98-1, AC-98-2, AC-98-3, AC-98-4 or AC-98-5 or a mixture thereof in combination or association with a pharmaceutically acceptable carrier. In particular, the present invention provides a pharmaceutical composition which comprises an effective amount of substantially pure AC-98-1, AC-98-2, AC-98-3, AC-98-4 or AC-98-5 or a mixture thereof and a pharmaceutically acceptable carrier.

The present invention also provides methods which may be used in treating bacterial infections in warm blooded animals which comprise administering to said animals an antibacterially effective amount of a substantially pure AC-98-1, AC-98-2, AC-98-3, AC-98-4 or AC-98-5 or a mixture thereof. Warm blooded animals includes humans.

DETAILED DESCRIPTION OF THE INVENTION

New substantially pure glycopeptide antibiotics AC-98-1, AC-98-2, AC-98-3, AC-98-4 and AC-98-5 are obtained from a complex AC-98 antibiotic mixture which is produced by aerobic fermentation of the culture (*Streptomyces hygroscopicus*) NRRL 3085 using the conditions as described in U.S. Pat. No. 3,495,004. This culture is maintained in the culture collection of Wyeth-Ayerst Research, Pearl River, N.Y. as culture number AC-98. A viable culture of this microorganism has been deposited, with the ARS Culture Collection, Fermentation Laboratory, Northern Regional Research Center, U.S. Department of Agriculture, 1815 North University Street, Peoria, Ill. 61604 and has been added to its permanent collection and assigned the strain designation NRRL 3085. Another suitable producing strain of *Streptomyces hygroscopicus* is NRRL 4600 (NRRL30439)

Cultivating of (*Streptomyces hygroscopicus*) NRRL 3085 and recovering mixtures of AC-98 antibiotics following silica gel and weakly acidic cation exchange resin chromatography is described in U.S. Pat. No. 3,495,004, incorporated herein by reference. The mixtures of AC-98 antibiotics from eleven like cultivations are combined, dissolved in water and butanol and evaporated to a residue which is further heated in methanol, centrifuged and collected as a AC-98 antibiotic mixture following washing with methanol and acetone. Separating the AC-98 antibiotic mixture into substantially pure AC-98-1, AC-98-2, AC-98-3, AC-98-4 or AC-98-5 is described in the present application.

Experimental efforts showed that the AC-98 mixture could not be effectively separated into substantially pure AC-98-1, AC-98-2, AC-98-3, AC-98-4 and AC-98-5 using reverse phase HPLC on C-18 columns which included Dynamax and Phenomenex C-18 columns (60A pore size, 5 or 8 μm particle size) using acetonitrile/water or methanol/water (both with adjusted pHs) as the solvents. Surprisingly, however, the separation resolution was accomplished by using YMC ODS-A columns (120A pore size, 5 or 10 μm particle size). As determined experimentally, the HPLC is performed with C18 reverse phase columns (YMC ODS-A, 120A pore size) using mixtures of acetonitrile or methanol in water containing small amounts of trifluoroacetic acid to control the acidity in the range of pH 3.5 and 5.5. The purification of the substantially pure antibiotics AC-98-1, AC-98-2, AC-98-3, AC-98-4, and AC-98-5 from the AC-98 antibiotic mixture is finally achieved by dissolving the AC-98 mixture in water or water/methanol mixture and subjecting the resulting solution to reverse phase HPLC.

Separating the substantially pure AC-98-1, AC-98-2, AC-98-3, AC-98-4 or AC-98-5 each from the others is accomplished using reverse phase HPLC on a C18 column (YMC ODS-A, 8 μm particle size, 20×250 mm) using a mobile phase consisting of a gradient from about 11% to about 25% by volume of acetonitrile in water containing about 0.02% trifluoroacetic. The flow rate of the mobile phase is maintained constant at 9 ml/minute and the effluent monitored by UV absorbance at 226 nm. Substantially pure AC-98-5 is further separated using reverse phase HPLC and a mobile phase gradient of about 40% to about 60% methanol in water containing about 0.02% trifluoroacetic acid.

Substantially pure glycopeptide antibiotics AC-98-1, AC-98-2, AC-98-3, AC-98-4 and AC-98-5 of this invention are defined as having, a purity of at least 85% when separated each from the others, as determined by high pressure liquid chromatography(HPLC). Preferably, substantially pure AC-98-1 is obtained with a purity of at least 92%, substantially pure AC-98-2 is obtained with a purity of at least 94%, substantially pure AC-98-3 is obtained with a purity of at least 89%, substantially pure AC-98-4 is obtained with a purity of at least 91% and substantially pure AC-98-5 is obtained with a purity of at least 89%.

The substantially pure glycopeptide antibiotics AC-98-1, AC-98-2, AC-98-3, AC-98-4, and AC-98-5 are isolated, purified and characterized from the AC-98 antibiotic mixture by dissolving the mixture in water or a water/methanol mixture and subjecting the resulting solution to reverse phase chromatography. Typically the chromatography is performed with C18 reverse phase media using mixtures of acetonitrile or methanol in water containing small amounts of organic acids, such as trifluoroacetic acid to control the acidity in the range of pH 3.5 and 5.5.

Cultivation of suitable producing strains of *Streptomyces hygroscopicus* may be carried out in a wide variety of suitable liquid culture media. Media which are useful for the production of AC-98 glycopeptide antibiotics include an assimilable source of carbon, such as dextrin, dextrose, sucrose, molasses, starch, glycerol, etc; an assimilable source of nitrogen such as protein, protein hydrolysate, polypeptides, amino acids, corn steep liquor, etc; and inorganic anions and cations, such as potassium, sodium, ammonium, calcium, sulfate, carbonate, phosphate, chloride, etc. Trace elements such as zinc, cobalt, iron, boron, molybdenum, copper, etc., are supplied as impurities of other constituents of the media. Aerobic conditions include aeration in tanks and bottles supplied by forcing sterile air through or onto the surface of the fermenting medium. Further agitation in tanks is provided by a mechanical impeller. An antifoam agent such as polypropylene glycol may be added as needed. In general, cultivating a suitable producing strain of *Streptomyces hygroscopicus* in a suitable culture medium is continued for about 24 to about 240 hours to produce a mixture of AC-98 antibiotics containing AC-98-1, AC-98-2, AC-98-3, AC-98-4 and AC-98-5. In particular, suitable liquid culture media are listed in Table A.

Culture Preservation

Cultures may be preserved as frozen whole cells (frozen vegetative mycelia, FVM) at −70° C. Glycerol may be added to cells grown for 24–48 hours in TSBG (Tryptic soy broth [Difco] supplemented with 20 g/L glucose) to a final concentration of 20%. The suspension may then be aliquoted to cryovials and frozen.

Inoculum Development and Growth of Organisms for Preparation of Frozen Stock Cultures Fermentations may be inoculated from "seed" stage cells grown in TSBG medium. Inoculum cells may be grown in various configurations depending on the fermentation scale, such as in test tubes containing 10 ml medium, shake-flasks containing 25, 50, 250 or 500 ml medium or in 10-liter fermentor. Primary seeds (tube, flask) may be inoculated from FVM at 0.2–5.0% and incubated on rotary shaker at 30° C. for 24–48 hours. Primary seeds may be used for inoculation of shake-flask and ten-liter fermentors. A second stage, ten-liter TSBG seed fermentor may be used for inoculation of 300-liter fermentations. Seed fermentors may be operated at 30° C., 500 rpm with 1 vvm air for 24–48 hours.

Shake-flask fermentations may be performed at 30° C. on a gyro-rotary shaker operating at 250 rpm (2" stroke) for from 3–5 days. Ten-liter fermentations may be performed at 30° C. for 3–5 days at 30° C., at 400–800 rpm with 1 vvm airflow. Fermentation at 300 liters may be performed similarly with agitation at 170–200 rpm. A polypropylene glycol antifoam, such as Macol P2000 may be added to fermentor medium at 0.2–2.0%. Three hundred-liter fermentations with medium BPM17statgal employ galactose at 8 g/L rather than the smaller scale concentration of 20 g/L.

LC/MS Analysis of Glycopeptide Antibiotics

The molecular weights of new substantially pure AC-98 glycopeptide antibiotics may be determined using a Hewlett-Packard API-electrospray LC/MS system with an HP 5989B Mass Spectrometer, HP 59987A API-Electrospray, HP 1090 series II HPLC and HP ChemStation data system with HP G1047A LC/MS software and UV detection at 226 nm. The MS electrospray may be performed in positive mode with a scan range of 400~1700 m/z.

Optional Procedure for Isolation of a Mixture of AC-98 Glycopeptide Antibiotics

Optionally, glycopeptide antibiotics of the AC-98 complex may be isolated from fermentations by passing supernatant through a column containing methacrylate resin XAD-7. The mixture of glycopeptide antibiotics of the AC-98 complex retained on the column may then be eluted by a mixed solvent of acetonitrile in water containing a small amount of acid. After solvent is evaporated under reduce pressure, the individual compounds may be purified by reverse phase chromatography. Typically, the chromatography is performed with C18 reverse phase media using mixtures of acetonitrile or methanol in water with small amount of acid for pH control, the preferred acid being trifluoroacetic acid.

Substantially pure glycopeptide antibiotics AC-98-1, AC-98-2, AC-98-3, AC-98-4, and AC-98-5 derive their utility from their antibacterial activity. In particular the substantially pure antibiotics AC-98-1, AC-98-2, AC-98-3, AC-98-4 and AC-98-5 are active against methicillin-susceptible and methicillin-resistant strains of staphylococci, against penicillin-susceptible and penicillin-resistant streptococci, and against vancomycin-susceptible and vancomycin-resistant enterococci. Further, for example, these compounds may be used in the suppression of bacterial infections, as a topical antibacterial agent and as a general disinfectant for laboratories.

TABLE A

Composition of fermentation media

| Component | BPM17 | BPM17stat | BPM17stat-gal | BPM17stat-man | BPM27 | BPM27-man |
|---|---|---|---|---|---|---|
| Pharmamedia (Traders) | 10 g/L | 20 g/L | 20 g/L | 20 g/L | 20 g/L | 20 g/L |
| Glucose | 40 g/L | 60 g/L | 60 g/L | 60 g/L | 60 g/L | 60 g/L |
| Galactose | — | — | 20 g/L | — | — | — |
| Mannose | — | — | — | 2 g/L | 2 g/L | — |
| CaCO$_3$ (Mississippi Lime) | 5 g/L | 5 g/L | 5 g/L | 5 g/L | — | — |
| CaCO$_3$ (Gamaco) | — | — | — | — | 15 g/L | 15 g/L |

In therapeutic use, the substantially pure glycopeptide antibiotics AC-98-1, AC-98-2, AC-98-3, AC-98-4, and AC-98-5 of this invention may be administered in the form of conventional pharmaceutical compositions appropriate for the intended use. Such compositions may be formulated so as to be suitable for oral, parenteral or topical administration. The substantially pure glycopeptide antibiotics AC-98-1, AC-98-2, AC-98-3, AC-98-4, and AC-98-5 may be combined in admixture with a nontoxic pharmaceutical carrier, which carrier may take a variety of forms, depending on the form of preparation desired for administration, ie. oral, parenteral, or topical.

When the substantially pure glycopeptide antibiotics AC-98-1, AC-98-2, AC-98-3, AC-98-4, and AC-98-5 are employed for the above utility, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example from about 10 to 50% of sugar, and elixirs containing, for example from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 0.05 up to about 90% of the substantially pure glycopeptide antibiotics AC-98-1, AC-98-2, AC-98-3, AC-98-4, and AC-98-5 in combination with the carrier, more usually between about 5% and 60% by weight.

An antibacterially effective amount of substantially pure glycopeptide antibiotics AC-98-1, AC-98-2, AC-98-3, AC-98-4 or AC-98-5 from about 0.5 mg/k body weight to about 200.0 mg/kg of body weight should be administered one to five times per day via any topical routes of administration including but not limited to oral, parenteral (including subcutaneous, intravenous, intramuscular, intrasternal injection or infusion techniques), by inhalation spray, or rectally, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sec, diet, mode and time of administration, rate of excretion, drug combination, the severity of the particular condition, and the host undergoing therapy.

Additionally, the antibacterially effective amount of the substantially pure glycopeptide antibiotics AC-98-1, AC-98-2, AC-98-3, AC-98-4 or AC-98-5 may be administered at a dosage and frequency without inducing side effects commonly experienced with conventional antibiotic therapy which could include hypersensitivity, neuromuscular blockade, vertigo, photosensitivity, discoloration of teeth, hematologic changes, gastrointestinal disturbances, ototoxicity, and renal, hepatic, or cardiac impairment. Further the frequency and duration of dosage may be monitored to substantially limit harmful effects to normal tissues caused by administration at or above the antibacterially effective amount of the substantially pure glycopeptide antibiotics AC-98-1, AC-98-2, AC-98-3, AC-98-4 or AC-98-5.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the stand-point of ease of preparation and administration are solid compositions, particularly tablets and hard-filled or liquid-filled capsules. Oral administration of the compound is preferred.

These substantially pure glycopeptide antibiotics AC-98-1, AC-98-2, AC-98-3, AC-98-4, and AC-98-5 may also be administered parenterally or intraperitoneally. Solutions or suspensions of these active compounds as a free base or pharmacologically acceptable salt can be prepared in water suitably mixed with a surfactant such as hydroxy propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microrganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention will be further described in conjunction with the following non-limiting examples.

EXAMPLE 1

Preparation of a Mixture of AC-98 Antibiotics

A mixture of AC-98 antibiotics is prepared following the fermentation description in Example 3 of U.S. Pat. No. 3,495,004 wherein the antibiotic containing eluate is concentrated and further purified by passing through a column of deactivated silica gel followed by a weakly acidic cation exchange resin, IRC-50. Elution of the resin by acidic aqueous solution, followed by evaporation in vacuo affords a mixture of glycopeptide antibiotics AC-98. The mixture of antibiotics from eleven individually isolated fermentation batches are combined to afford 23.626 g of a mixture of AC-98 antibiotics which is dissolved in 500 ml of water containing a minimum volume of butyl alcohol and filtered. The filtrate is evaporated in vacuo with the further addition of butyl alcohol and continuous evaporation while removing excess water to afford a residue. To the residue is added 100 ml of methyl alcohol followed by heating to the boil and centrifuging to a solid. The solid is washed with methyl alcohol then acetone followed by centrifuging to afford 19.841 g of a mixture of AC-98 antibiotics as a solid after rewashing with acetone and drying.

The mixture of AC-98 antibiotics is analyzed by HPLC to contain mainly five components, designated as AC-98-1 (17%), AC-98-2 (19%), AC-98-3 (15%), AC-98-4 (29%), and AC-98-5 (4%). The relative quantity of each antibiotic is calculated based on the integration area at 226 nm. Referring to the remaining 16% of the mixture of AC-98 antibiotics, approximately 15% belong to components which have a different UV spectra and less than 1% further minor components of AC-98 antibiotics. The analysis is performed by HPLC on a C18 column (YMC ODS-A, 5 µm particle size, 4.6×150 mm). The mobile phase, monitored by UV detector at 226 nm, is a gradient of acetonitrile (10% to 50%) in water containing 0.01% trifluoroacetic acid over 22 minutes at a flow rate of 1 ml per minute. The relative quantity of each glycopeptide antibiotic is calculated based on the integration area at 226 nm.

EXAMPLE 2

Substantially Pure Glycopeptide Antibiotics AC-98-1, AC-98-2, AC-98-3, and AC-98-4 from a Mixture of AC-98 Antibiotics A mixture of AC-98 antibiotics(180 mg) from Example 1 is dissolved in water (1 ml) and subjected to reverse phase HPLC on a C18 column (YMC ODS-A, 8 µm particle size, 20×250 mm). The mobile phase consisting of a gradient from 11% to 25% by volume of acetonitrile in water containing 0.02% trifluoroacetic acid over 45 minutes. The flow rate of the mobile phase is maintained constant at 9 ml/minute and the effluent monitored by UV absorbance at 226 nm. Individually collected fractions having the same retention times by HPLC are pooled and upon evaporation infrared, proton nuclear magnetic resonance, and carbon 13 magnetic resonance spectra recorded. The substantially pure glycopeptide antibiotics AC-98-1, AC-98-2, AC-98-3, AC-98-4 and a mixture as trifluoroacetate salts are isolated and listed in Table 1.

TABLE 1

| COMPONENT | RETENTION TIME | WEIGHT COLLECTED* |
|---|---|---|
| Substantially Pure AC-98-1 | 20 MINUTES | 35 mg |
| Substantially Pure AC-98-2 | 28 MINUTES | 29 mg |
| Substantially Pure AC-98-3 | 32 MINUTES | 25 mg |
| Substantially Pure AC-98-4 | 37 MINUTES | 64 mg |
| Mixture | 43 MINUTES | 13 mg |

*trifluoroacetate salt

EXAMPLE 3

Isolation of Substantially Pure Glycopeptide Antibiotic AC-98-5 Trifluoroacetate The mixture from Table 1 (13 mg) eluted at 43 minutes is dissolved in water (200 µl) and subjected to reverse phase HPLC on a C18 column (YMC ODS-A, 8 µm particle size, 20×250 mm). The mobile phase is a gradient of methanol (40% to 60%) in water containing 0.02% trifluoroacetic acid over 40 minutes at a flow rate of 9 ml/minute. The major peak centers at 29 minutes, as monitored by UV detector at 226 nm, and upon evaporation infrared, proton nuclear magnetic resonance and carbon 13 magnetic resonance spectra are recorded. The substantially pure AC-98-5 (5 mg) is isolated as a trifluoroacetate salt.

The purities of the five substantially pure glycopeptide antibiotics separated by methods described in Examples 1–3, are determined by HPLC analyses (226 nm) to be:

AC98-1—92%
AC98-2—94%
AC98-3—89%
AC98-4—91%
AC98-5—89%

The substantially pure glycopeptide antibiotics AC-98-1, AC-98-2, AC-98-3, AC-98-4, and AC-98-5 are tested in the following standard pharmacological test procedures.

BIOLOGICAL ACTIVITY

The in vitro antibacterial activity of substantially pure glycopeptide antibiotics AC-98-1, AC-98-2, AC-98-3, AC-98-4, and AC-98-5 from Examples 2 and 3 is determined against a spectrum of bacteria by a standard agar dilution method. Mueller-Hinton agar containing 5% sheep blood and two-fold decreasing concentrations of substantially pure glycopeptide antibiotics AC-98-1, AC-98-2, AC-98-3, AC-98-4, and AC-98-5 from Examples 2 and 3 are poured into petri dishes. The agar surfaces are inoculated with 1 to $5\times10^4$ colony forming units of bacteria by means of a Steers replicating device. The lowest concentration of antibiotic that inhibited the growth of a bacterial strain after 18 hours incubation is recorded as the minimal inhibitory concentration for that strain. The results are given in Table II.

TABLE II

In vitro antibacterial activity of substantially pure antibiotics AC-98-1, AC-98-2, AC-98-3, AC-98-4, and AC-98-5 from Examples 2 and 3

| | MIC (mg/mL) | | | | |
|---|---|---|---|---|---|
| Organism | AC-98-1 | AC-98-2 | AC-98-3 | AC-98-4 | AC-98-5 |
| *Staphylococcus aureus* (NEMC-89-4) | >128 | 64 | 8 | 8 | 4 |
| *Staphylococcus aureus* (ID-2371) | >128 | 128 | 8 | 8 | 4 |
| *Staphylococcus aureus* (ID-2727) | >128 | 64 | 8 | 8 | 4 |
| *Staphylococcus aureus* (SMITH) | 128 | 64 | 8 | 8 | 4 |
| *Staphylococcus aureus* (ID-3105) | 128 | 64 | 8 | 8 | 4 |
| *Staphylococcus aureus* (ID-4379) | 128 | 64 | 8 | 4 | 4 |
| *Staphylococcus aureus* (ATCC 29213) | 128 | 64 | 8 | 8 | 4 |

TABLE II-continued

In vitro antibacterial activity of substantially pure antibiotics AC-98-1, AC-98-2, AC-98-3, AC-98-4, and AC-98-5 from Examples 2 and 3

| Organism | MIC (mg/mL) | | | | |
|---|---|---|---|---|---|
| | AC-98-1 | AC-98-2 | AC-98-3 | AC-98-4 | AC-98-5 |
| *Staphylococcus hemolyticus* (ID-4061) | 128 | 32 | 8 | 4 | 4 |
| Staph Coagulase Neg (ID-3135) | 128 | 32 | 8 | 4 | 2 |
| Staph Coagulase Neg (ID-3276) | 128 | 64 | 4 | 4 | 2 |
| Staph Coagulase Neg (ID-3120) | 128 | 64 | 8 | 8 | 2 |
| Staph Coagulase Neg (ID-3941) | 64 | 32 | 4 | 2 | 2 |
| Staph Coagulase Neg (4615) | >128 | 128 | 8 | 8 | 4 |
| *Enterococcus faecalis* (ID-4168) | >128 | >128 | 64 | 64 | 16 |
| *Enterococcus faecalis* (ID-1829) | >128 | 128 | 64 | 64 | 32 |
| *Enterococcus faecalis* (ID-2131) | >128 | >128 | 128 | 64 | 32 |
| *Enterococcus faecalis* (12201) | >128 | >128 | 64 | 32 | 16 |
| *Enterococcus faecalis* (ATCC 29212) | >128 | >128 | 64 | 64 | 16 |
| *Enterococcus faecium* (12202) | >128 | 128 | 64 | 64 | 32 |
| *Enterococcus faecium* (ID-3301) | >128 | >128 | 64 | 64 | 16 |
| *Enterococcus faecium* (ID-4133) | 128 | 32 | 16 | 8 | 4 |
| *Enterococcus faecium* (ID-3953) | >128 | 128 | 64 | 64 | 32 |
| *Streptococcus pyogenes* (ID-3187) | >32 | 64 | 8 | 8 | 2 |
| *Streptococcus pneumoniae* (ID-4444) | >32 | >64 | 8 | 4 | 2 |
| *Streptococcus pneumoniae* (GC1889) | | | 4 | 4 | |
| *Pseudomonas aeruginosa* (ATCC 27853) | >128 | >128 | >128 | >128 | >128 |
| *Morganella morganii* (VGH 84-11) | >128 | >128 | >128 | >128 | >128 |
| *Escherichia coli* (J2175) | >128 | 64 | >128 | 128 | 64 |
| *Escherichia coli* (J2445) | 64 | 32 | 4 | 4 | 1 |
| *Escherichia coli* (ATCC 25922) | >128 | 64 | >128 | >128 | 128 |
| *Bacillus subtilis* (Bacto) | >128 | >128 | 16 | 16 | 8 |
| *Micrococcus luteus* (ATCC 9341) | 64 | 16 | 2 | 2 | 1 |

The in vivo antibacterial activity of substantially pure glycopeptides AC-98-1, AC-98-2, AC-98-3, AC-98-4, and AC-98-5 is established by infecting female CD-1 mice from Charles River Laboratories, weighing 20+/−2 g each, intraperitoneally with $6.5 \times 10^5$ CFU/0.5 ml of broth of *Staphylococcus aureus* Smith. The mice are treated intravenously, 30 minutes before infection with the indicated dose of the test compound in 0.2 ml of water. The results of this test are given in Table III.

TABLE III

In vivo antibacterial activity of substantially pureglycopeptide antibiotics AC-98-1, AC-98-2, AC-98-3, AC-98-4, and AC-98-5 from Examples 2 and 3

| Compound | $ED_{50}$ (iv, mg/kg) *Staphylococcus aureus* |
|---|---|
| AC-98-1 | 20 |
| AC-98-2 | >32 |
| AC-98-3 | 3.8 |
| AC-98-4 | 2.6 |
| AC-98-5 | 0.6 |

We claim:
1. A substantially pure compound having the structure

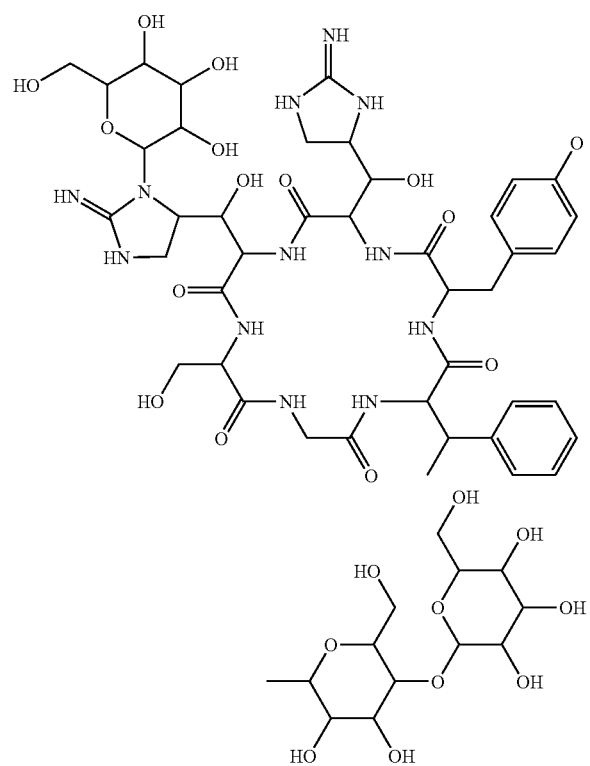

or pharmaceutically acceptable salts, thereof.

2. A substantially pure compound according to claim 1 and having the structure

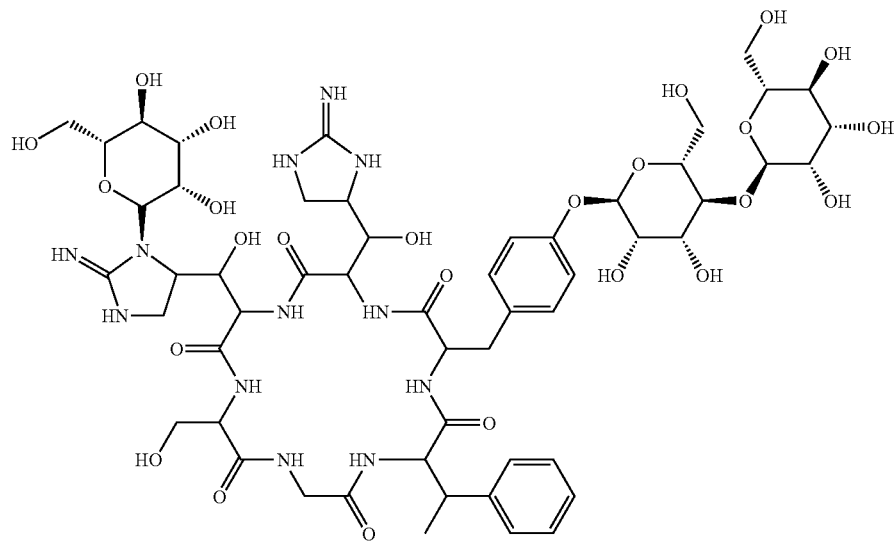

3. A method for treating bacterial infections in warm blooded animals which comprises providing to said animals an antibacterially effective amount of a compound according to claim 2.

4. A pharmaceutical composition which comprises a compound according to claim 2 in association with a pharmaceutically acceptable carrier.

5. A substantially pure compound having the structure

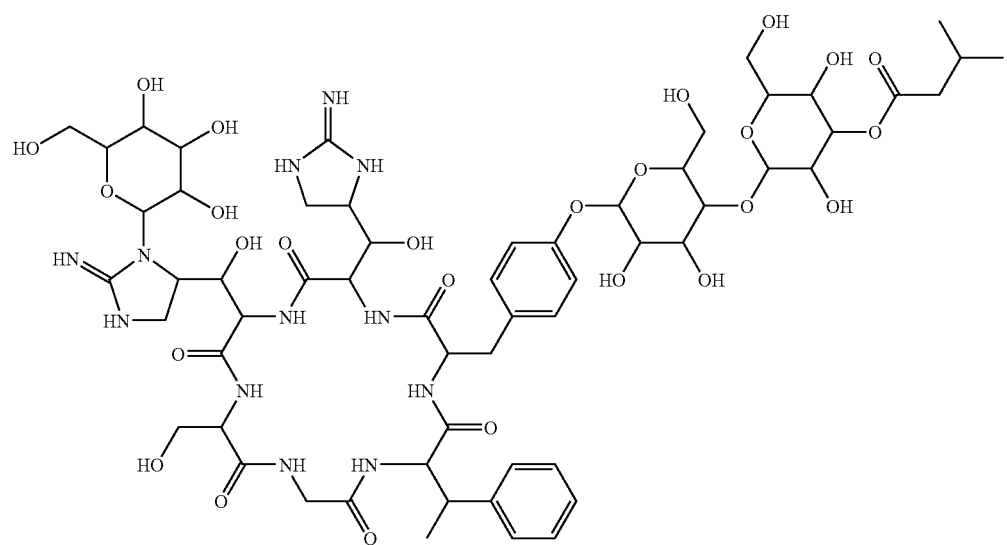

or pharmaceutically acceptable salts thereof.

6. A substantially pure compound according to claim 5 having the structure

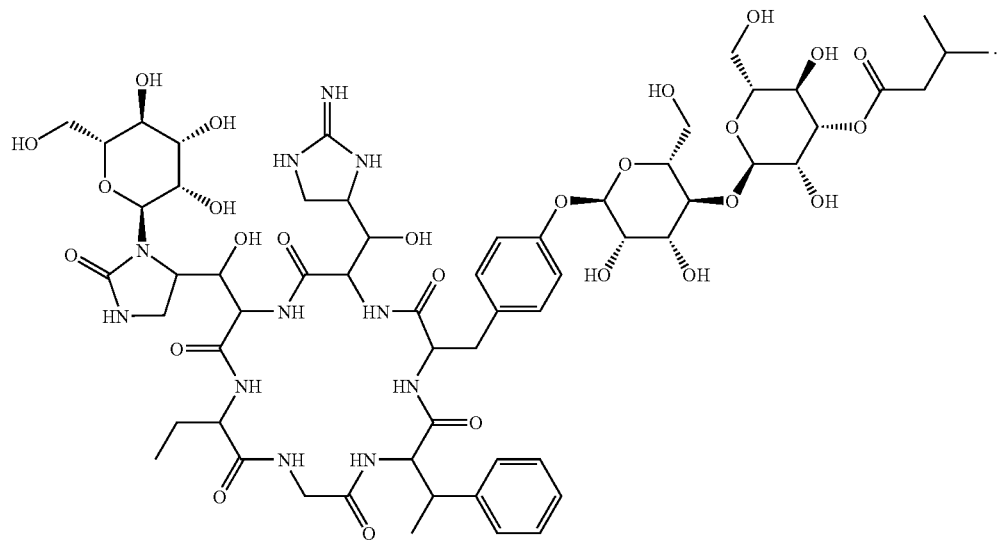

7. A method for treating bacterial infections in warm blooded animals which comprises providing to said animals an antibacterially effective amount of a compound according to claim 6.

8. A pharmaceutical composition which comprises a compound according to claim 6 in association with a pharmaceutically acceptable carrier.

9. A substantially pure compound having the structure

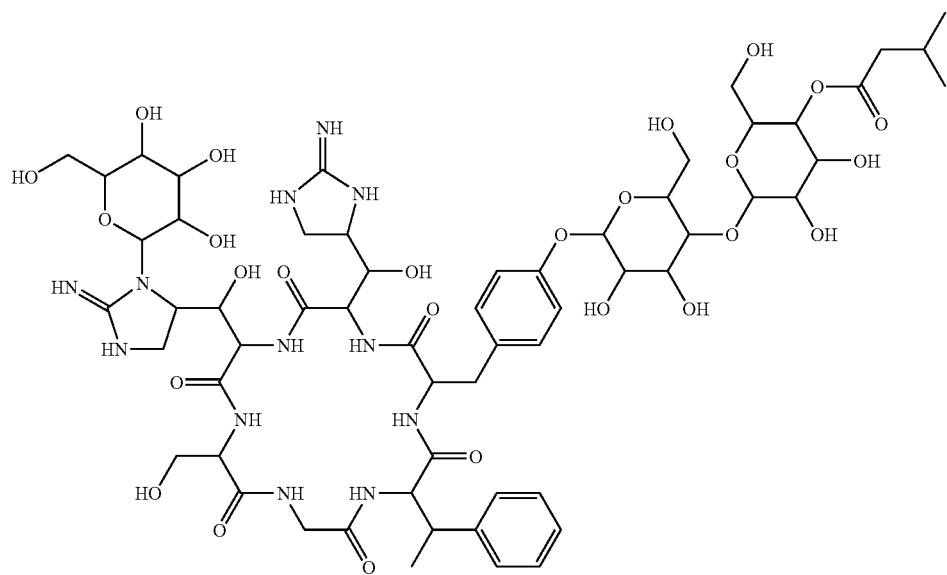

or pharmaceutically acceptable salts thereof.

10. A substantially pure compound according to claim 9 having the structure

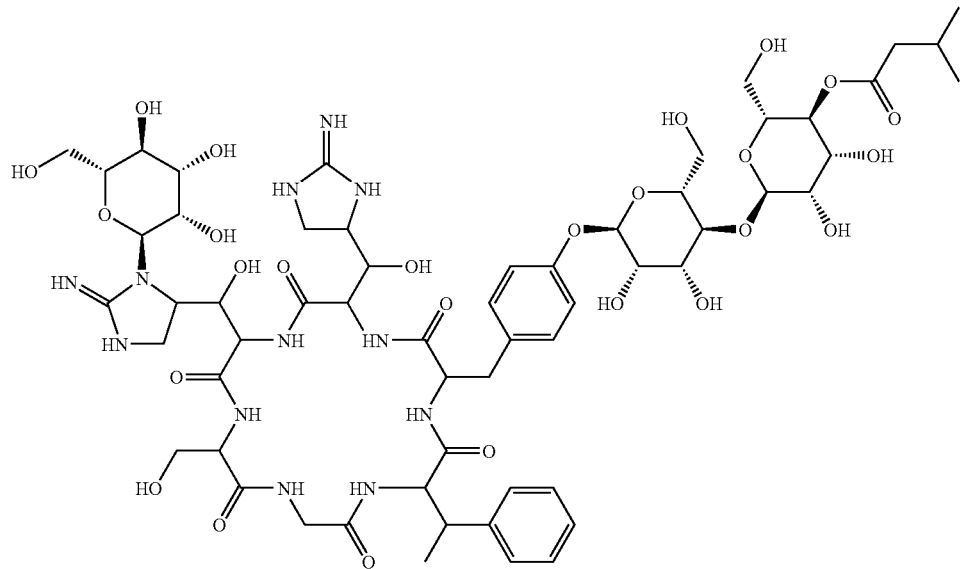

or pharmaceutically acceptable salts thereof.

11. A method for treating bacterial infections in warm blooded animals which comprises providing to said animals an antibacterially effective amount of a compound according to claim 10.

12. A pharmaceutical composition which comprises a compound according to claim 10 in association with a pharmaceutically acceptable carrier.

* * * * *